US011896656B2

(12) United States Patent
Ahl et al.

(10) Patent No.: US 11,896,656 B2
(45) Date of Patent: Feb. 13, 2024

(54) METHODS FOR PROVIDING A HOMOGENOUS SOLUTION OF LYOPHILIZED MUTANT DIPTHERIA TOXIN IN DIMETHYLSULFOXIDE

(71) Applicant: Merck Sharp & Dohme LLC, Rahway, NJ (US)

(72) Inventors: Patrick Leonard Ahl, West Point, PA (US); Akhilesh Bhambhani, Doylestown, PA (US); Christopher Jon Farrell, Wayne, PA (US); Patrick McHugh, Pipersville, PA (US); Morrisa C. Jones, Upper Darby, PA (US); Daniel D. Roth, Coopersburg, PA (US); Jessica R. Sinacola, Collegeville, PA (US); Justin Stanbro, Sellersville, PA (US); Matthew P. Watson, Ottsville, PA (US); Emily Wen, Harleysville, PA (US); Michael A. Winters, Doylestown, PA (US)

(73) Assignee: MERCK SHARP & DOHME LLC, Rahway, NJ (US)

( * ) Notice: Subject to any disclaimer, the term of this patent is extended or adjusted under 35 U.S.C. 154(b) by 203 days.

(21) Appl. No.: 17/049,266

(22) PCT Filed: Apr. 25, 2019

(86) PCT No.: PCT/US2019/029038
§ 371 (c)(1),
(2) Date: Oct. 20, 2020

(87) PCT Pub. No.: WO2019/212844
PCT Pub. Date: Nov. 7, 2019

(65) Prior Publication Data
US 2021/0252126 A1     Aug. 19, 2021

Related U.S. Application Data

(60) Provisional application No. 62/664,648, filed on Apr. 30, 2018.

(51) Int. Cl.
A61K 39/08     (2006.01)
A61K 39/09     (2006.01)
A61K 39/39     (2006.01)
A61K 39/00     (2006.01)

(52) U.S. Cl.
CPC ............ *A61K 39/092* (2013.01); *A61K 39/39* (2013.01); *A61K 2039/6037* (2013.01)

(58) Field of Classification Search
CPC .................................................. A61K 39/092
See application file for complete search history.

(56) References Cited

U.S. PATENT DOCUMENTS

| | | | |
|---|---|---|---|
| 6,146,902 A | 11/2000 | McMaster | |
| 6,517,526 B1 * | 2/2003 | Tamari | A61L 2/26 604/408 |
| 7,709,001 B2 | 5/2010 | Hausdorff et al. | |
| 8,808,707 B1 | 8/2014 | Siber | |
| 9,669,084 B2 | 6/2017 | Siber | |
| 10,406,220 B2 | 9/2019 | Siber et al. | |
| 2007/0042031 A1 | 2/2007 | MacLachlan et al. | |
| 2007/0231340 A1 | 10/2007 | Hausdorff et al. | |
| 2009/0010966 A1 | 1/2009 | Davis et al. | |
| 2011/0195086 A1 | 8/2011 | Caulfield et al. | |
| 2011/0201791 A1 | 8/2011 | Prasad | |
| 2012/0045479 A1 | 2/2012 | Sievers et al. | |
| 2015/0190521 A1 | 7/2015 | Biemans et al. | |
| 2015/0202309 A1 | 7/2015 | Emini et al. | |
| 2016/0009768 A1 | 1/2016 | Davis et al. | |
| 2016/0252300 A1 | 9/2016 | Bhambhani et al. | |
| 2016/0324948 A1 | 11/2016 | Gu et al. | |
| 2016/0324950 A1 * | 11/2016 | Anderson | A61K 39/40 |
| 2017/0220463 A1 | 8/2017 | Malina et al. | |
| 2018/0099039 A1 | 4/2018 | Emini et al. | |

FOREIGN PATENT DOCUMENTS

| | | | |
|---|---|---|---|
| CN | 102068690 A | | 5/2011 |
| EP | 3096786 B1 | | 7/2021 |
| WO | 200038711 A2 | | 7/2000 |
| WO | 2006110352 A2 | | 10/2006 |
| WO | 2006110381 A1 | | 10/2006 |
| WO | 2007127665 A2 | | 11/2007 |
| WO | 2008045852 A2 | | 4/2008 |
| WO | 2008118752 A2 | | 10/2008 |
| WO | 2009009629 A1 | | 1/2009 |
| WO | 2010080484 A1 | | 7/2010 |
| WO | 2010080486 A2 | | 7/2010 |
| WO | 2011/041003 | * | 4/2011 |

(Continued)

OTHER PUBLICATIONS

Arditi et al., Three-Year Multicenter Surveillance of Pneumococcal Meningitis in Children: Clinical Characteristics, and Outcome Related to Penicillin Susceptibility and Dexamethasone Use, Pediatrics, 1998, 1087-1097, 102(5).
Lei et al., Quantification of free polysaccharide in meningococcal polysaccharide-diphtheria toxoid conjugate vaccines, Dev. Biol., 2000, Abstract—1/1, 103.
MMWR, Prevention of Pneumococcal Disease: Recommendations of the Advisory Committee on Immunization Practices (ACIP), Centers for Disease Control and Prevention, Jan. 15, 1997, 46(RR-8).

(Continued)

*Primary Examiner* — Albert M Navarro
(74) *Attorney, Agent, or Firm* — Steven C. Pageau; Anna L. Cocuzzo

(57) ABSTRACT

A method is described for reconstituting lyophilized mutant diphtheria toxin in dimethyl sulfoxide for use in producing pneumococcal capsular polysaccharide mutant diphtheria toxin conjugates.

13 Claims, 10 Drawing Sheets

(56) References Cited

FOREIGN PATENT DOCUMENTS

| | | | |
|---|---|---|---|
| WO | 2011041003 A2 | 4/2011 | |
| WO | WO2011041003 | * | 4/2011 |
| WO | 2011100151 A1 | 8/2011 | |
| WO | 2011151760 A2 | 12/2011 | |
| WO | 2012078482 A1 | 6/2012 | |
| WO | 2014097099 A2 | 6/2014 | |
| WO | 2015110940 A2 | 7/2015 | |
| WO | 2015110941 A2 | 7/2015 | |
| WO | 2015110942 A2 | 7/2015 | |
| WO | 2016113644 A1 | 7/2016 | |
| WO | 2016178123 A1 | 11/2016 | |
| WO | 2017013548 A1 | 1/2017 | |
| WO | 2017085586 A1 | 5/2017 | |
| WO | 2017085602 A1 | 5/2017 | |
| WO | 2018134693 A1 | 7/2018 | |
| WO | 2018144438 A1 | 8/2018 | |
| WO | 2018144439 A1 | 8/2018 | |
| WO | 2018156465 A1 | 8/2018 | |
| WO | 2018156467 A1 | 8/2018 | |
| WO | 2018156468 A1 | 8/2018 | |
| WO | 2018156491 A1 | 8/2018 | |
| WO | 2018212846 A1 | 11/2018 | |
| WO | 2019036313 A1 | 2/2019 | |
| WO | 2019050813 A1 | 3/2019 | |
| WO | 2019050814 A1 | 3/2019 | |
| WO | 2019050815 A1 | 3/2019 | |
| WO | 2019050816 A1 | 3/2019 | |
| WO | 2019050818 A1 | 3/2019 | |
| WO | 2019083865 A1 | 5/2019 | |
| WO | 2019139692 A2 | 7/2019 | |
| WO | 2019212842 A1 | 11/2019 | |
| WO | 2019212844 A1 | 11/2019 | |
| WO | 2019212846 A1 | 11/2019 | |
| WO | 2019217183 A1 | 11/2019 | |
| WO | 2019236435 A1 | 12/2019 | |
| WO | 2020121159 A1 | 6/2020 | |
| WO | 2020131763 A2 | 6/2020 | |
| WO | 2020208502 A1 | 10/2020 | |
| WO | 2020247299 A1 | 12/2020 | |
| WO | 2020247301 A1 | 12/2020 | |

OTHER PUBLICATIONS

Shivu, Bhavana, Distinct /J-Sheet Structure in Protein Aggregates Determined by ATR-FTIR Spectroscopy, Biochemistry, 2013, 5176-5183, 52.

Lei, Q.P. et al., Quantification of Free Polysaccharide in Meningococcal Polysaccharide-Diphtheria Toxoid Conjugate Vaccines, Dev. Biol., 2000, 259-264, 103.

Steven P. Schwendeman et al., Stabilization of tetanus and diphtheria toxoids against moisture-induced aggregation, Proc. Natl. Acad. Sci. USA, 1995, 11234-11238, 92.

Nagaki, Aiichiro et al., Fast Micromixing and Flow Synthesis, Nagare: Journal of Japan Society of Fluid Mechanics, Mar. 9, 2015, 34.

* cited by examiner

```
                                    Polysaccharide (Ps) powder
                                              │
     (Serotype 18C only)            ┌─────────────────────┐
    ┌─────────────────┐             │   Ps dissolution    │
    │  Acid hydrolysis │◄────────────│ 0.45-micron filtration│      (Serotype 19A only)
    └─────────────────┘             │   Homogenization    │
            │                       │ 0.22-micron filtration│◄──────
            └──────────────────────►│                     │
     Diptheria toxin                │   Ultrafiltration 1 │
      (DT) solution                 │    Ps activation    │
    ┌─────────────────┐             │   Ultrafiltration 2 │
    │ DT ultrafiltration│            │   Ps lyophilization │
    │ 0.5/0.2-micron  │             │ Redissolution in DMSO│
    │   filtration    │             │                     │
    │ DT lyophilization│             │                     │
    │Redissolution in DMSO├───────►  │   Ps-DT mixing      │
    └─────────────────┘             │ Conjugation reaction│
                                    │   Quench reaction   │
     (Serotype 19F only)            │      Dilution       │
    ┌─────────────────┐             │   Ultrafiltration 3 │
    │  0.22-micron    │◄────────────│                     │
    │   filtration    │             │   Ultrafiltration 4 │────────┐
    │   Incubation    │◄────────────│                     │        │
    └─────────────────┘             │ 0.22-micron filtration│    ┌──▼──────────┐
                                    │ Dilution and dispense│◄───│0.5/0.2-micron│
                                    └─────────────────────┘    │  filtration  │
                                              │                └──────────────┘
                                              ▼                (Serotype 18C only)
                                    Drug Substance, ≤-60°C

FIG.8
```

METHODS FOR PROVIDING A HOMOGENOUS SOLUTION OF LYOPHILIZED MUTANT DIPTHERIA TOXIN IN DIMETHYLSULFOXIDE

BACKGROUND OF THE INVENTION

(1) Field of the Invention

The present invention relates to a method for reconstituting lyophilized mutant diphtheria toxin (mDT) in anhydrous dimethyl sulfoxide for use in producing pneumococcal capsular polysaccharide:mDT conjugates.

(2) Description of Related Art

*Streptococcus pneumoniae*, one example of an encapsulated bacterium, is a significant cause of serious disease world-wide. In 1997, the Centers for Disease Control and Prevention (CDC) estimated there are 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97. The multivalent pneumococcal polysaccharide vaccines that have been licensed for many years have proved invaluable in preventing pneumococcal disease in adults, particularly, the elderly and those at high-risk. However, infants and young children respond poorly to unconjugated pneumococcal polysaccharides. Bacterial polysaccharides are T-cell-independent immunogens, eliciting weak or no response in infants. Chemical conjugation of a bacterial polysaccharide immunogen to a carrier protein converts the immune response to a T-cell-dependent one in infants. Diphtheria toxoid (DTx, a chemically detoxified version of diphtheria toxin (DT)) and DT have been described as carrier proteins for bacterial polysaccharide immunogens due to the presence of T-cell-stimulating epitopes in their amino acid sequences.

Thus, polysaccharide-protein conjugate vaccines, comprising bacterial capsular polysaccharides conjugated to carrier proteins have been developed and additional ones are in development. Examples of developed conjugate vaccines include the *Haemophilus influenzae* type b (Hib) conjugate vaccine (e.g., HIBTITER®) as well as conjugate vaccines against *Streptococcus pneumoniae* (e.g., PREVNAR® and PREVNAR 13®) and *Neisseria meningitidis* (e.g., MENJUGATE®).

BRIEF SUMMARY OF THE INVENTION

The present invention provides a method for preparing a homogenous solution of mutant diphtheria toxin (mDT) in anhydrous dimethyl sulfoxide (DMSO) in which there is no detectable beta-sheet mediated aggregation of the mDT as determined by Fourier-transform infrared spectroscopy or dynamic light scattering for up to six hours following preparation of the homogenous solution. The homogenous solution is useful for preparing a plurality of *Streptococcus pneumoniae* polysaccharide-mDT conjugates, each conjugate comprising polysaccharides of a particular serotype and which may be used to produce multivalent pneumococcal immunogenic compositions having particular combinations of conjugates for use in vaccines.

The present invention provides a method for making a homogeneous solution of mutant diphtheria toxin (mDT) in anhydrous DMSO, the method comprising (a) providing a dried composition of mDT; and (b) reconstituting the dried composition in anhydrous DMSO by adding the anhydrous DMSO to the dried composition over a time period of two minutes or less and mixing for at least 10 seconds to provide the homogenous solution comprising the mDT.

In particular embodiments of the method, the dried composition of the mDT is prepared by a sublimative drying process selected from lyophilization and radiant energy vacuum (REV) dehydration from an aqueous solution of the mDT. In a further embodiment, the sublimative drying process comprises freezing the aqueous solution in the form of cakes or lyosphere beads. In another embodiment, the sublimative drying is bulk drying performed in a container selected from the group consisting of metal tray, plastic tray, plastic bag, and class I tubing vials.

In particular embodiments, the dried composition is prepared by sublimative drying of an aqueous solution comprising the mDT to produce the dried composition, wherein the aqueous solution further comprises sucrose and a buffer, and the sublimative drying is selected from lyophilization and radiant energy vacuum (REV) dehydration.

In particular embodiments, the buffer is a Histidine, Succinate, MES, MOPS, HEPES, or Acetate buffer in a pH range of 5.0-7.0. In particular embodiments, the buffer is a Phosphate or a Citrate buffer in a pH range of 5.0-7.0.

In particular embodiments, the aqueous solution comprises about 0.5% (w/v) or more sucrose. In particular embodiments, the aqueous solution comprises about 4% to 8% (w/v) sucrose.

In particular embodiments, the dried composition has a final moisture content of about 6% or less. In particular embodiments, the dried composition has a final moisture content of about 5% or less. In particular embodiments, the dried composition has a final moisture content of about 4% or less. In particular embodiments, the dried composition has a final moisture content of about 3% or less. In particular embodiments, the dried composition has a final moisture content of about 2% or less.

In particular embodiments, the aqueous solution comprises the mDT at a concentration of about 6 to 12 mg/mL. In particular embodiments, the aqueous solution comprises the mDT at a concentration of about 6, 9, 10, or 12 mg/mL.

In particular embodiments of the method, the reconstituting in step (b) is performed in eight minutes or less. In particular embodiments, the reconstituting is performed in six minutes or less. In particular embodiments, the reconstituting is performed in four minutes or less. In particular embodiments, the reconstituting is performed in two minutes or less. In particular embodiments, the reconstituting is performed in about two minutes. In particular embodiments, the reconstituting is performed in one minute or less.

In particular embodiments, the mixing in step (b) is instead performed in 120 minutes or less. In particular embodiments, the mixing is instead performed in 90 minutes or less. In particular embodiments, the mixing is instead performed in 60 minutes or less. In particular embodiments, the mixing is instead performed in 30 minutes or less. In particular embodiments, the mixing is instead performed in 10 minutes or less. In particular embodiments, homogenous solution comprising the mDT is used for conjugation to activated polysaccharides within six hours or less following the reconstituting.

The present invention further provides a method for providing a homogeneous solution of mutant diphtheria toxin (mDT) in anhydrous dimethyl sulfoxide (DMSO) having no detectable beta-sheet mediated aggregation, the method comprising: (a) providing a dried composition of the mDT; and (b) reconstituting the dried composition in anhydrous DMSO by adding the anhydrous DMSO to the dried composition over a time period of two minutes or less and mixing to provide a homogenous solution comprising the mDT wherein the homogenous solution comprises no detectable beta-sheet mediated aggregation as determined by Fourier-transform infrared spectroscopy or dynamic light scattering.

In a further embodiment, the homogenous solution comprises no detectable beta-sheet mediated aggregation for up to one hour following reconstitution. In a further embodiment, the homogenous solution comprises no detectable beta-sheet mediated aggregation for up to two hours following reconstitution. In a further embodiment, the homogenous solution comprises no detectable beta-sheet mediated aggregation for up to three hours following reconstitution. In a further embodiment, the homogenous solution comprises no detectable beta-sheet mediated aggregation for up to four hours following reconstitution. In a further embodiment, the homogenous solution comprises no detectable beta-sheet mediated aggregation for up to five hours following reconstitution. In a further embodiment, the homogenous solution comprises no detectable beta-sheet mediated aggregation for up to six hours following reconstitution.

In particular embodiments of the method, the dried composition of the mDT is prepared by a sublimative drying process selected from lyophilization and radiant energy vacuum (REV) dehydration from an aqueous solution of the mDT. In a further embodiment, the sublimative drying process comprises freezing the aqueous solution in the form of cakes or lyosphere beads prior to the sublimative drying process. In another embodiment, the sublimative drying comprises bulk drying performed in a container selected from the group consisting of metal tray, plastic tray, plastic bag, and class I tubing vials.

In particular embodiments, the dried composition has a final moisture content of about 6% or less. In particular embodiments, the dried composition has a final moisture content of about 5% or less. In particular embodiments, the dried composition has a final moisture content of about 4% or less. In particular embodiments, the dried composition has a final moisture content of about 3% or less. In particular embodiments, the dried composition has a final moisture content of about 2% or less.

In particular embodiments, the dried composition is prepared by sublimative drying of an aqueous solution comprising the mDT to produce the dried composition, wherein the aqueous solution further comprises sucrose and a buffer, and the sublimative drying is selected from lyophilization and radiant energy vacuum (REV) dehydration.

In particular embodiments, the aqueous solution comprises about 0.5% (w/v) or more sucrose. In particular embodiments, the aqueous solution comprises about 4% to 8% (w/v) sucrose.

In particular embodiments, the buffer is a Histidine, Succinate, MES, MOPS, HEPES, or Acetate buffer in a pH range of 5.0-7.0.

In particular embodiments, the buffer is a Phosphate or a Citrate buffer in a pH range of 5.0-7.0.

In particular embodiments, the aqueous solution comprises the mDT at a concentration of about 6 to 12 mg/mL.

In particular embodiments, the aqueous solution comprises the mDT at a concentration of about 6, 9, 10, or 12 mg/mL.

In particular embodiments of the method, the reconstituting in step (b) is instead performed in eight minutes or less. In particular embodiments, the reconstituting is instead performed in six minutes or less. In particular embodiments, the reconstituting is instead performed in four minutes or less. In particular embodiments, the reconstituting is instead performed in two minutes or less. In particular embodiments, the reconstituting is instead performed in about two minutes. In particular embodiments, the reconstituting is instead performed in one minute or less.

In particular embodiments, the mixing in step (b) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less. In particular embodiments, homogenous solution comprising the mDT is used for conjugation to activated polysaccharides within six hours or less following the reconstituting.

The present invention further provides a method for making a composition comprising a *Streptococcus pneumoniae* polysaccharide covalently linked to a mutant diphtheria toxin (mDT), comprising the steps of (a) providing a first dried composition comprising activated *Streptococcus pneumoniae* polysaccharides from one or more *Streptococcus pneumoniae* serotypes and a second dried composition comprising mDT; (b) separately reconstituting the first dried composition and the second dried composition in dimethyl sulfoxide (DMSO) and mixing to provide a first homogenous solution comprising the one or more activated polysaccharides and a second homogenous solution comprising the mDT; (c) combining the first homogenous solution with the second homogenous solution to produce a mixture; and (d) adding a reducing agent to the mixture to produce a conjugate solution comprising mDT conjugated to one or more polysaccharides of one or more *Streptococcus pneumoniae* serotypes, characterized in that the first dried composition is reconstituted in anhydrous DMSO and the second dried composition is reconstituted in anhydrous DMSO by adding the anhydrous DMSO to the second dried composition over a time period of two minutes or less and mixing to provide the homogenous solution comprising the mDT or wherein the improvement is that the first dried composition is reconstituted in anhydrous DMSO and the second dried composition is reconstituted in anhydrous DMSO by adding the anhydrous DMSO to the second dried composition over a time period of two minutes or less and mixing to provide the homogenous solution comprising the mDT.

In particular embodiments of the method, the first and second dried compositions are prepared by a sublimative drying process selected from lyophilization and radiant energy vacuum (REV) dehydration. In a further embodiment, the sublimative drying process comprises freezing the first and second aqueous solutions in the form of cakes or lyosphere beads prior to the sublimative drying process. In another embodiment, the sublimative drying process comprises bulk drying performed in a container selected from the group consisting of metal tray, plastic tray, plastic bag, and class I tubing vials.

In particular embodiments, each of the first and second dried compositions has a final moisture content of about 6% or less. In particular embodiments, each of the first and second dried compositions has a final moisture content of about 5% or less. In particular embodiments, each of the first and second dried compositions has a final moisture content of about 4% or less. In particular embodiments, each of the first and second dried compositions has a final moisture content of about 3% or less. In particular embodiments, each of the first and second dried compositions has a final moisture content of about 2% or less.

In particular embodiments, the first and second dried compositions are prepared by a sublimative drying of a first aqueous solution comprising activated Streptococcus pneumoniae polysaccharides from one, two, or more Streptococcus pneumoniae serotypes and a second aqueous solution comprising the mDT to produce the first and second dried compositions, wherein the first and second aqueous solutions further comprise about 0.5% (w/v) or more sucrose and a buffer, and wherein the sublimative drying is selected from lyophilization or radiant energy vacuum (REV) dehydration.

In particular embodiments, the buffer is a Histidine, Succinate, MES, MOPS, HEPES, or Acetate buffer in a pH range of 5.0-7.0.

In particular embodiments, the buffer is a Phosphate or a Citrate buffer in a pH range of 5.0-7.0.

In particular embodiments, the first and second aqueous solutions comprise about 0.5% (w/v) or more sucrose. In particular embodiments, the first aqueous solution comprises about 4% to 6% (w/v) sucrose and the second aqueous solution comprises about 4% to 8% (w/v) sucrose.

In particular embodiments, the first aqueous solution comprises the polysaccharide at a concentration of about 6 to 9 mg/mL and the second aqueous solution comprises the mDT at a concentration of about 6 to 12 mg/mL. In particular embodiments, the first aqueous solution comprises the polysaccharide at a concentration of about 6 or 9 mg/mL and the second aqueous solution comprises the mDT at a concentration of about 6, 9, 10, or 12 mg/mL.

In particular embodiments of the method, the reconstituting in step (b) is instead performed in eight minutes or less. In particular embodiments, the reconstituting is instead performed in six minutes or less. In particular embodiments, the reconstituting is instead performed in four minutes or less. In particular embodiments, the reconstituting is instead performed in two minutes or less. In particular embodiments, the reconstituting is instead performed in about two minutes. In particular embodiments, the reconstituting is instead performed in one minute or less.

In particular embodiments, the mixing in step (b) is performed in 120 minutes or less. In particular embodiments, the mixing is performed in 90 minutes or less. In particular embodiments, the mixing is performed in 60 minutes or less. In particular embodiments, the mixing is performed in 30 minutes or less. In particular embodiments, the mixing is performed in 10 minutes or less.

In particular embodiments, each conjugate solution comprises polysaccharide conjugated to the mDT at a ratio from about 0.6 to about 1.3 polysaccharide to mDT on a weight to weight basis. In particular embodiments, each conjugate solution comprises polysaccharide conjugated to the mDT at a ratio from about 0.9 to about 1.5 polysaccharide to mDT on a weight to weight basis. In particular embodiments, each conjugate solution comprises polysaccharide conjugated to the mDT at a ratio from about 0.6 to about 1.5 polysaccharide to mDT on a weight to weight basis.

In particular embodiments, the conjugate solution comprises a free polysaccharide concentration that is less than about 15% of the total polysaccharide in the solution. In particular embodiments, the conjugate solution comprises a free polysaccharide concentration that is less than about 10% of the total polysaccharide in the solution.

In particular embodiments, the conjugate has an mDT lysine loss value of greater than five (mole/mole).

In particular embodiments, each conjugate solution comprises polysaccharide conjugated to the mDT at a ratio from about 0.6 to about 1.3 polysaccharide to mDT on a weight to weight basis, free polysaccharide concentration that is less than about 15% of the total polysaccharide in the solution, and the conjugate has a mDT lysine loss value of greater than five (mole/mole).

In particular embodiments, the one or more Streptococcus pneumoniae serotypes are selected from the group consisting of Streptococcus pneumoniae serotypes 1, 2, 3, 4, 5, 6A, 6B, 6C, 6D, 6E, 6G, 6H, 7F, 7A, 7B, 7C, 8, 9A, 9L, 9N, 9V, 10F, 10A, 10B, 10C, 11F, 11A, 11B, 11C, 11D, 11E, 12F, 12A, 12B, 13, 14, 15F, 15A, 15B, 15C, 16F, 16A, 17F, 17A, 18F, 18A, 18B, 18C, 19F, 19A, 19B, 19C, 20A, 20B, 21, 22F, 22A, 23F, 23A, 23B, 24F, 24A, 24B, 25F, 25A, 27, 28F, 28A, 29, 31, 32F, 32A, 33F, 33A, 33B, 33C, 33D, 33E, 34, 35F, 35A, 35B, 35C, 36, 37, 38, 39, 40, 41F, 41A, 42, 43, 44, 45, 46, 47F, 47A, 48, CWPS1, CWPS2, and CWPS3.

In particular embodiments, the one or more Streptococcus pneumoniae polysaccharides are activated by reacting with an oxidizing agent to provide the activated polysaccharides in step (a).

In any one of the embodiments herein the mutant diphtheria toxoid is $CRM_{197}$.

In particular embodiments, the conjugate solution is sterile filtered.

BRIEF DESCRIPTION OF THE DRAWINGS

FIG. 8 shows a general scheme for making mutant diphtheria toxin (mDT) polysaccharide (Ps) conjugates.

DETAILED DESCRIPTION OF THE INVENTION

I. Definitions

Figure 1:
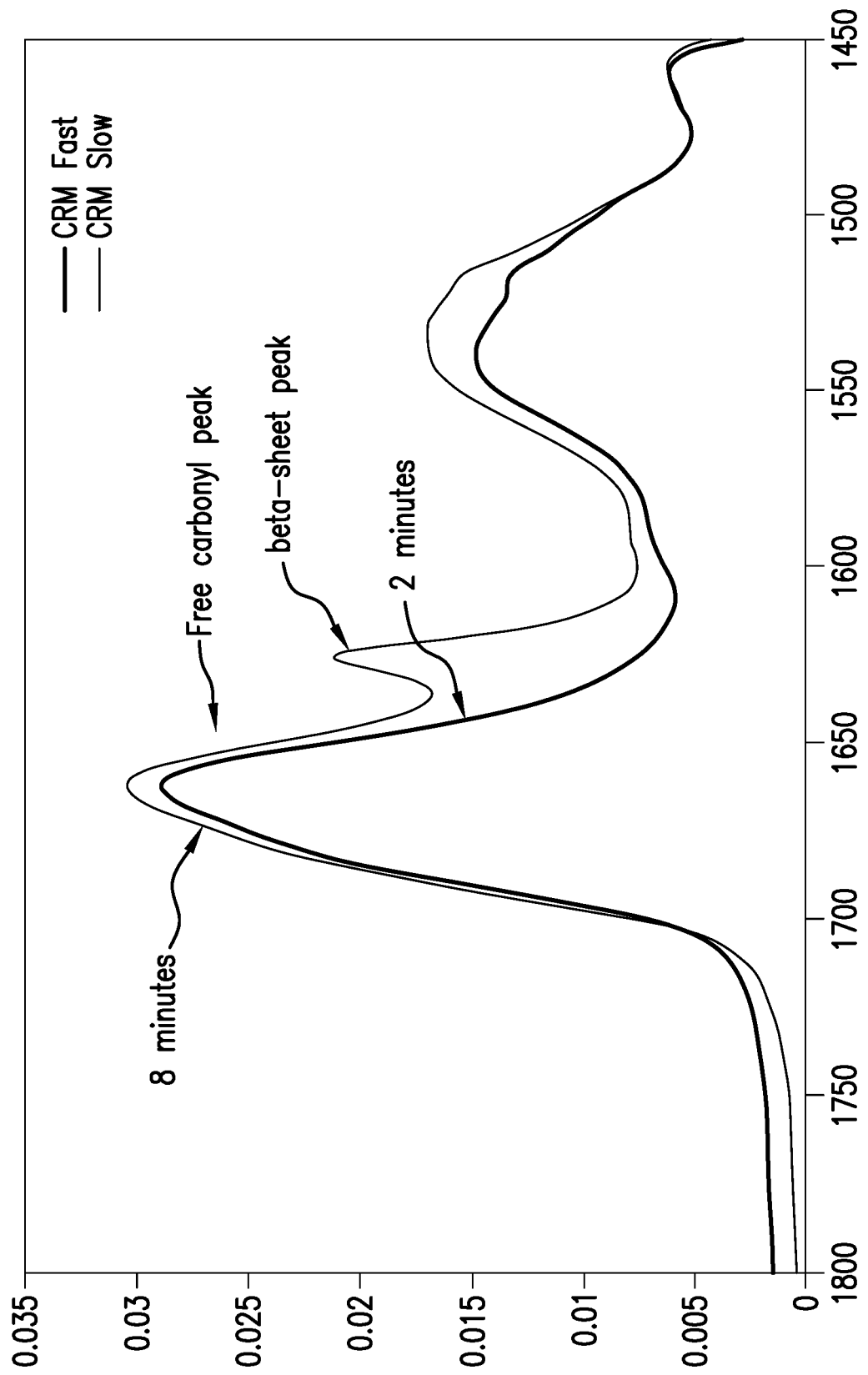
FIG. 1 shows FTIR spectra of $CRM_{197}$ with fast (two minutes) vs. slow (eight minutes) reconstitution in anhydrous DMSO.

As used herein, the term "polysaccharide" (Ps) is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like. Depending on the context, Ps may singular or plural.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular S. pneumoniae polysaccharide protein conjugates and no other S. pneumoniae polysaccharide protein conjugates from a different serotype.

As defined herein, the terms "precipitation", "precipitate", "particulate formation", "clouding", and "aggregation" may be used interchangeably and are meant to refer to any physical interaction or chemical reaction which results in the agglomeration of a polysaccharide-protein conjugate. The process of aggregation (e.g., protein aggregation) may be induced by numerous physicochemical stresses, including heat, pressure, pH, agitation, shear forces, freeze-thawing, dehydration, heavy metals, phenolic compounds, silicon oil, denaturants and the like.

As used herein, the term "reconstituting" or "reconstitution" refers to adding a liquid to a dried material to dissolve the dried material to provide a solution of the material dissolved therein. However, the solution provided by the reconstitution may have concentration gradients or layers of the dissolved material therein. Therefore, following reconstitution, the solution is physically agitated to provide a homogenous solution of the reconstituted material.

As used herein, the term "mixing" is use to refer to the physical agitation of a solution by shaking, stirring, rocking, rotating, or the like.

As used herein, the term "homogenous solution" refers to a solution in which all components are thoroughly mixed such there are no concentration gradients or layers between the components in the solution.

As used herein, a "lyosphere" is a discrete particle of lyophilized material, for example, taking the form of a bead or sphere or other shape. A lyosphere may also be referred to as a lyoparticle sphereon, or lyobead. In some embodiments, the lyosphere diameter is from about 2 to about 12 mm, preferably from 2 to 8 mm, such as from 2.5 to 6 mm or 2.5 to 5 mm. In some embodiments, the volume of the lyosphere is from about 20 to 550 µL, preferably from 20 to 100 µL, such as from 20 to 50 µL. In embodiments wherein the lyosphere is not substantially spherical, the size of the lyosphere can be described with respect to its aspect ratio, which is the ratio of the longer dimension to the shorter dimension. The aspect ratio of the lyospheres can be from 0.5 to 2.5, preferably from 0.75 to 2, such as from 1 to 1.5.

As used herein, an "immunogenic composition" may be a multivalent composition containing one or more antigens conjugated to one or more mDT, e.g., $CRM_{197}$. In certain embodiments of the invention, the antigen is a saccharide from an encapsulated bacteria. In such compositions, the saccharides are composed of long chains of sugar molecules that resemble the surface of certain types of bacteria. Encapsulated bacteria include, but are not limited to, *Streptococcus pneumoniae, Neisseria meningitides* and *Haemophilus influenzae* type b. The antigens may be from the same organism or may be from different organisms. In preferred embodiments of the invention, the antigens are *Streptococcus pneumoniae* capsular polysaccharides.

As used herein, the term "radiant energy vacuum (REV) dehydration" also refers to microwave vacuum drying (MVD).

II. The Process

The present invention provides a method or process for producing multivalent pneumococcal polysaccharide-protein conjugates that may be used as anti-pneumococcal vaccines, in which mutant diphtheria toxin (mDT) is reconstituted in anhydrous dimethyl sulfoxide (DMSO) over a rapid time span of 2 minutes or less to provide a homogenous solution that is combined with a homogenous solution of activated polysaccharides reconstituted in anhydrous DMSO under conditions that result in formation of a conjugate composition having low levels of free polysaccharide (e.g., less than 15% free polysaccharide) with no detectable beta-sheet mediated aggregation.

The inventors discovered that during reconstitution of the mDT, the length of time in which an organic solvent such as DMSO is added to the dried mDT and the length of time the reconstituted mDT is then stored or maintained prior to conjugation have an impact on the secondary structure of the mDT and thus the yield of conjugates having the desired molecular weight and ratio of mDT to polysaccharide conjugated thereto. The invention is exemplified herein with $CRM_{197}$, a non-toxic variant (i.e., toxoid) of diphtheria toxin. As shown in FIGS. 1-7, the time for reconstituting dried mDT in anhydrous DMSO under fast addition conditions, e.g., adding the anhydrous DMSO to the dried mDT within less than eight minutes or about two minutes or less provides a reconstituted mDT solution in which the mDT is completely unfolded and there is no detectable beta-sheet formation as determined by Fourier-transform infrared spectroscopy (FTIR) or dynamic light scattering (DLS). Further discovered was that having any detectable water present in the DMSO and/or having mDT at a final concentration of mDT greater than 12 mg/mL results in beta-sheet mediated aggregation. Therefore, in a preferred embodiment of the invention, anhydrous DMSO is added to the dried mDT over a time period that is less than eight minutes, preferably less than five minutes, and more preferably two minutes or less; and the mDT is maintained at a concentration at or less than 10 mg/mL or 12 mg/mL or less, in particular embodiments, at about 6 mg/mL.

In particular embodiments, to ensure complete dissolution of the dried mDT and polysaccharide, a first homogenous solution comprising mDT and a second homogenous solution comprising the activated polysaccharides may be mixed for 120 minutes or less. In particular embodiments, the mixing may be 90 minutes or less. In particular embodiments, the mixing may be 60 minutes or less. In particular embodiments, the mixing may be 30 minutes or less. In particular embodiments, the mixing may be 10 minutes or less. In particular embodiments, the second homogenous solution comprising the mDT is in the DMSO solution for about six hours or less prior to combining with the first homogenous solution comprising the polysaccharides. The inventors have discovered that maintaining the mDT in DMSO for more than six hours results in detectable beta-sheet mediated aggregation of the mDT. Thus, in particular embodiments, the mDT is maintained in the DMSO for six hours or less.

FIG. 8 shows a general scheme for making mDT polysaccharide conjugates in which the mDT is prepared as taught herein.

In general, purified pneumococcal capsular polysaccharide (Ps) powder for each of the serotypes is separately dissolved in water to provide a solution that is 045-micron filtered except for solutions comprising Ps from serotype 19A. All solutions comprising Ps from any of the serotypes disclosed herein, except serotype 19A, are homogenized to reduce the molecular mass of the Ps. Serotype 18C is size-reduced by acid hydrolysis at 90° C. or more. Serotype 19A is not size reduced due to its relatively low starting size. Homogenization pressure and number of passes through the homogenizer are controlled to serotype-specific targets to achieve a serotype-specific molecular mass. The polysaccharides are each 0.22-micron filtered and then concentrated and diafiltered against water in Ultrafiltration Step 1 using a 10 kD ultrafiltration membrane with open channel (type 5) to produce diafiltrate 1.

Diafiltrate 1 may then be adjusted to a serotype-specific temperature (between 4-22° C.) and pH (4-5) with a buffer, for example, sodium acetate, to minimize polysaccharide size reduction during the activation step. Polysaccharide activation is performed via periodate oxidation. For serotype 4, prior to activation, the solution is incubated at approximately 50° C. and pH 4 to partially deketalize the polysaccharide. Polysaccharide activation is initiated with the addition of a sodium metaperiodate solution. The amount of sodium metaperiodate added is serotype-specific, ranging from approximately 0.1 to 0.5 moles of sodium metaperiodate per mole of polysaccharide repeating unit. The serotype-specific charge of sodium metaperiodate is selected to achieve a target level of polysaccharide activation (moles aldehyde per mole of polysaccharide repeating unit).

In Ultrafiltration Step 2, for all serotype solutions, with the exception of solutions comprising serotypes 5 and 7F, the activated polysaccharide may be diafiltered and then concentrated by tangential flow ultrafiltration using a 10 kD ultrafiltration membrane with open channel (type 5) to produce diafiltrate 2. At the end of the diafiltration, the diafiltrate 2 may be concentrated to a target of 15 g Ps/L. Solutions comprising serotypes 5 and 7F may be diafiltered against a buffer, for example 10 mM sodium acetate. Preferably, the ultrafiltration for all serotype solutions is conducted at 2-8° C.

Diafiltrate 2 is then diluted in water with sucrose added to make a solution having a final concentration of about 4 to 12 mg/mL polysaccharide and 0.5% to 6% (w/v) sucrose and subjected to a sublimative drying process to produce dried polysaccharide, preferably having a final moisture content of 6% or less. In particular embodiments, the compositions have final moisture contents of about 5% or less. In particular embodiments, the compositions have final moisture contents of about 4% or less. In particular embodiments, the compositions have final moisture contents of about 3% or less. In particular embodiments, the compositions have final moisture contents of about 2% or less. The amount of sucrose that is added to the solution prior to lyophilization is serotype specific and may range from 3.0 to 5.0% (w/v) prior to lyophilization. In particular embodiments, two or more polysaccharides may be dried together to produce a dried polysaccharide mixture.

Solutions comprising purified mDT are diafiltered against 2 mM phosphate, pH 7.0 buffer using a 5 kDa tangential flow ultrafiltration membrane and then filtered through a 0.22-micron filter. The filtered solutions are diluted in water with sucrose for a final concentration of about 6 to 12 mg/mL mDT and 4 to 10% (w/v) sucrose and subjected to a sublimative drying process to produce dried mDT, preferably having a final moisture content of 6% or less. In particular embodiments, the compositions have final moisture contents of about 5% or less. In particular embodiments, the compositions have final moisture contents of about 4% or less. In particular embodiments, the compositions have final moisture contents of about 3% or less. In particular embodiments, the compositions have final moisture contents of about 2% or less.

The sublimative drying process for the polysaccharide and mDT solutions may include lyophilization or radiant energy vacuum (REV) dehydration.

The dried polysaccharide or dried polysaccharide mixture and dried mDT are separately reconstituted or redissoluted in anhydrous dimethyl sulfoxide (DMSO) to provide homogeneous solutions of each. In particular embodiments, the mDT is reconstituted at a concentration of about 10 to 20 mg/mL or about 10 mg/mL. The inventors discovered using $CRM_{197}$ as a model that 1% (v/v) or more moisture in the DMSO will result in beta-sheet formation (See FIG. 5). Therefore, the present invention provides embodiments in which the moisture content of the DMSO is less than 1% (v/v) or in which the DMSO comprises no detectable moisture, for example, anhydrous DMSO or 100% (v/v) DMSO. The dried mDT is reconstituted by adding DMSO to the dried mDT over a time period of less than eight minutes, preferably in less than six minutes or less than four minutes, or most preferably in two minutes or less, or one minute or less. The inventors have also discovered using $CRM_{197}$ as a model that the shorter the addition time for adding DMSO to the dried mDT, the less formation of irreversible beta-sheet mediated aggregation based on Fourier-transform infrared spectroscopy (FTIR) and dynamic light scattering (DLS) analysis. As shown in FIG. 1, anhydrous DMSO addition time of two minutes results in no detectable formation of beta-sheet mediated aggregation. Therefore, in particular embodiments, the present invention provides for the reconstitution of mDT in DMSO containing less than 1% moisture or DMSO containing no detectable moisture, e.g., anhydrous or 100% (v/v) DMSO in which the addition of the said DMSO is added to the dried mDT over a time period of two minutes or less than two minutes to provide the reconstituted mDT at a concentration of 20 mg/mL or less or about 10 mg/mL or less. In particular embodiments, following reconstitution, the mixture may be mixed for up to 30 minutes to provide a homogenous solution of the mDT. However, in particular embodiments, the mixing may occur over time period of 120 minutes or less, 90 minutes or less, 60 minutes or less, 30 minutes or less, or 10 minutes or less. In particular embodiments, 500 mM sodium phosphate, pH 7.2, buffer is added to the homogenous solution comprising the mDT for a final concentration of 1.0 mM sodium phosphate.

The homogenous solution of mDT and homogenous solution of polysaccharide or two or more different polysaccharides are combined to provide a conjugation solution containing both the mDT and the polysaccharide or two or more different polysaccharide. Following reconstitution or redissolution in DMSO, the polysaccharide and mDT homogenous solutions are combined targeting a serotype-specific final polysaccharide concentration and polysaccharide to mDT ratio. In general, the mDT and polysaccharide are combined in amounts that will provide a final conjugated polysaccharide to mDT ratio from about 0.6 to 1.3 (w/w).

To effect the conjugation reaction, a solution of sodium cyanoborohydride in water is prepared and 1.0 meq of sodium cyanoborohydride (1.0 mole of sodium cyanoborohydride per mole of polysaccharide repeating unit) is added to the conjugation solution. The molarity of the sodium cyanoborohydride solution is based on a target amount of about 0.5% total water content of the solution during conjugation. The conjugation solution is allowed to react at serotype-specific temperature for a serotype-specific duration to produce an mDT:polysaccharide conjugate intermediate.

Next, a solution of sodium borohydride in water is prepared and 2.0 meq of sodium borohydride (relative to polysaccharide repeating units) is added to the conjugation solution. The molarity of the sodium borohydride solution is based on a target amount of about 1.0% total water content in the conjugation solution after borohydride addition. The conjugation solution is allowed to react for three hours (except for certain serotypes such as serotype 7F, in which the reaction time is for two hours) at ambient temperature to produce the mDT:polysaccharide conjugate.

To quench the conjugation reaction, the conjugation solution is diluted in a dilution step to 20% (v/v) or less DMSO by slowly adding the conjugation solution to a solution of 150 mM sodium chloride (150 mM sodium chloride with 0.025% (w/v) polysorbate 20 for conjugates comprising polysaccharides from particular serotypes to produce a quenched conjugate solution. In particular embodiments the temperature is maintained at 15° C. or less during the dilution step. After about an hour, a 1.5 M potassium phosphate, pH 6.0, solution may be added to the solution to a final concentration of 25 mM potassium phosphate. Conjugation performance may be assessed by overall polysaccharide and mDT consumption, conjugate polysaccharide to mDT ratio, and conjugate molecular weight.

In Ultrafiltration Step 3, the quenched conjugate solution may be concentrated to about 2.5 g/L and diafiltered against up to about 10 diavolumes of 150 mM sodium chloride or 25 mM potassium phosphate in 150 mM sodium chloride at 2-8° C. using a 30 kDa tangential flow ultrafiltration membrane to produce diafiltrate 3. The polysaccharide concentration in diafiltrate 3 from ultrafiltration step 3 may be determined by high performance size exclusion chromatography (HPSEC) ultraviolet multi-angle light scattering refractive index (UV-MALS-RI). For conjugates comprising polysaccharides from some serotypes such as serotype 19F, diafiltrate 3 may be filtered through a 0.22-micron filter to produce a filtrate that is subsequently incubated at 22° C. for about 120 hours.

In Ultrafiltration Step 4, diafiltrate 3 or filtrate from Ultrafiltration Step 3 may be concentrated to a polysaccharide concentration of about 2.5 g/L and diafiltered against 20 diavolumes of 10 mM L-histidine in 150 mM sodium chloride, pH 7.0 at 2-8° C. using a 300 kDa tangential flow ultrafiltration membrane to produce diafiltrate 4. For conjugates comprising polysaccharides from certain serotypes, e.g., serotype 7F, the conjugate may be diafiltered against a 100 kDa tangential flow ultrafiltration membrane; e.g., conjugates comprising serotype 6A, 6B, and 18C polysaccharides, may be concentrated to about 3.5 g/L and diafiltered against a buffer comprising 150 mM sodium chloride and 0.03% (w/v) polysorbate 20, pH 7.0, at 2-8° C. using a 300 kDa tangential flow ultrafiltration membrane to produce diafiltrate 4. Conjugates comprising serotype 7F, 19A, 19F and 23F polysaccharides may be concentrated to about 2.0 g/L and diafiltered against a buffer comprising 150 mM sodium chloride and 0.015% (w/v) polysorbate 20, pH 7.0, at 2-8° C. using a 300 kDa regenerated cellulose tangential flow ultrafiltration membrane to produce diafiltrate 4. The polysaccharide concentration in diafiltrate 2 may be determined by HPSEC UV-MALS-RI. The buffer may be 10-50 mM acetate, phosphate, TRIS, HEPES, or an amino acid buffer such as a histidine. In particular embodiments, the buffer is 10 mM L-histidine.

Diafiltrate 4 from Ultrafiltration Step 4 may be filtered through a 0.22-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, pH 7.0. This provides a Monovalent Bulk Conjugate intermediate (MBC) or monovalent drug substance. The MBC may be dispensed into aliquots and frozen at −60° C. to −80° C.

Diafiltrate 4 from Ultrafiltration Step 4 for conjugates comprising serotype 6A, 6B, and 18C polysaccharides may be filtered through a dual-membrane 0.5/0.2-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, 0.03% (w/v) polysorbate 20, pH 7.0. This provides an MBC or monovalent drug substance. The MBC may be dispensed into aliquots and frozen at −60° C. to −80° C.

Diafiltrate 4 for conjugates comprising serotype 7F, 19A, 19F, and 23F polysaccharides may be filtered through a 0.22-micron filter to produce a second filtrate. The polysaccharide concentration of the second filtrate may be determined by HPSEC UV-MALS-RI. If the polysaccharide concentration of the second filtrate is greater than 1.0 g/L, the second filtrate may be diluted to a polysaccharide concentration of 1.0 g/L with additional 10 mM L-histidine in 150 mM sodium chloride, 0.015% (w/v) polysorbate 20, pH 7.0. This provides an MBC or monovalent drug substance. The MBC may be dispensed into aliquots and frozen at −60° C. to −80° C.

III. Polysaccharides

Capsular polysaccharides from *Streptococcus pneumoniae* can be prepared by standard techniques known to those skilled in the art. For example, polysaccharides can be isolated from bacteria and may be sized to some degree by known methods (see, e.g., European Patent Nos. EP497524 and EP497525); and in particular embodiments, by microfluidisation accomplished using a homogenizer or by chemical hydrolysis. In one embodiment, *S. pneumoniae* strains are grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity and/or to improve filterability of subsequent conjugated products. In the present invention, capsular polysaccharides are prepared from one or more of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38.

IV. Mutant Diphtheria Toxin

In a particular embodiment of the present invention, $CRM_{197}$ is used as the mDT. $CRM_{197}$ is a non-toxic variant (i.e., toxoid) of diphtheria toxin (DT). In one embodiment, it is isolated from cultures of *Corynebacterium diphtheria* strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in *Pseudomonas fluorescens* using PFENEX EXPRESSION TECHNOLOGY (Pfenex Inc., San Diego, Calif.).

Other mDTs can be used, such as $CRM_{176}$, $CRM_{228}$, $CRM_{45}$ (Uchida et al., 1973, J Biol Chem 218:3838-3844); $CRM_{9}$, $CRM_{45}$, $CRM_{102}$, $CRM_{103}$ and $CRM_{107}$ and other mutats described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragments disclosed in U.S. Pat. No. 5,843,711.

V. Sublimative Drying

The aqueous compositions comprising polysaccharide of a specific *Streptococcus pneumoniae* serotype and compositions comprising a mDT may be separately dried using a sublimative process to provide a composition comprising dried mDT having a final moisture content of 6% or less and a composition comprising a dried polysaccharide of a specific *Streptococcus pneumoniae* serotype having a final moisture content of about 6% or less. Dried compositions may be prepared, for example, by a sublimative process such as lyophilization or radiant energy vacuum (REV) dehydration (microwave vacuum-drying) in a traveling wave format, Spray freeze-drying, Vacuum Drying, RF Drying etc. in a continuous or semi-continuous mode. See e.g., Encyclopedia of Agriculture, Food, and Biological Engineering. Marcel Dekker, Inc or Xu & Sunada, Chem Pharm Bull (Tokyo) 55(11):1545-50 (2007). The lyophilized formulation components may be in the form of a cake or a particle, e.g., a pellet, bead or sphere of lyophilized material, e.g., lyospheres. See e.g., A. S. Mujumdar (2007). Handbook of Industrial Drying. CRC Press.

Lyospheres can be made, for example, by loading an aliquot of an aqueous solution comprising one or more polysaccharide serotypes in the form of a droplet (e.g., about 20, 50, 100 or 250 microliters) onto a solid, flat surface in such a way that the droplet remains intact. In an embodiment of the invention, the surface is a plate, e.g., a metal plate, e.g. at a temperature of about −180° C. to about −196° C. or about −180° C. to about −273° C. For example, in an embodiment of the invention, the aqueous solution is loaded onto the surface by way of a dispensing tip. In an embodiment of the invention, the aqueous solution is dispensed at a dispensing speed of about 3 ml/min to about 75 ml/min, about 5 ml/min to about 75 ml/min; about 3 ml/min to about 60 ml/min, about 20 ml/min to about 75 ml/min; and about 20 ml/min to about 60 ml/min. In an embodiment of the invention, the aqueous solution that is dispensed is 250 microliters and the dispensing speed is between about 5 mL/min to about 75 mL/min, or wherein the aliquot is 100 microliters and the dispensing speed is between about 3 mL/min to about 60 mL/min. In an embodiment of the invention, the gap between a dispensing tip and the surface onto which the aqueous solution is dispensed is about 0.1 cm or more (e.g., about 0.5 cm or between 0.1 cm and 1 cm or between 0.1 cm and 0.75 cm). Once on the surface, the aqueous solution is frozen and then subjected to sublimative drying by lyophilization. Methods for making lyospheres are known in the art. See e.g., U.S. Pat. No. 5,656,597; WO2013066769; WO2014093206; WO2015057540; WO2015057541 or WO2015057548.

In an embodiment of the invention, the aqueous solution is lyophilized by radiant energy vacuum (REV) dehydration (microwave vacuum-drying). REV dehydration is a drying method done under reduced pressure, where the boiling point of water and the oxygen content of the atmosphere are lower. For example, in an embodiment of the invention, an aliquot of the aqueous solution is deposited as a single droplet onto a solid surface, wherein the temperature of the surface is at about −90° C. or below, in a manner that maintains droplet as a single droplet as it contacts and freezes on the surface as a frozen pellet; and applying microwave radiation to the frozen pellet under a pressure below atmospheric pressure to produce a dried pellet, such as a sphere. In another example, the aqueous solution is provided on a tray and subjected to microwave radiation under a pressure below atmospheric pressure to produce a dried cake. See, e.g., U.S. Pat. Nos. 4,389,794; 4,664,924; 4,809,596; 4,882,851.

VI. Polysaccharide Protein Conjugation

The purified polysaccharides are chemically activated to introduce functionalities capable of reacting with the mDT. Once activated, each capsular polysaccharide is separately conjugated to a mDT to form a glycoconjugate according to the method of the present invention.

In one embodiment, the chemical activation of the polysaccharides may be achieved by means described in U.S. Pat. Nos. 4,365,170; 4,673,574; and, 4,902,506. Briefly, the pneumococcal polysaccharide is reacted with an oxidizing agent, for example, a periodate-based oxidizing agent such as sodium periodate, potassium periodate, or periodic acid, resulting in random oxidative cleavage of vicinal hydroxyl groups to generate reactive aldehyde groups. Direct aminative coupling of the oxidized polysaccharide to primary amine groups on the mDT (mainly lysine residues) may be accomplished by reductive amination. For example, conjugation may be carried out in an aqueous solution or in an organic solvent such as dimethyl sulfoxide (DMSO). See, e.g., US2015/0231270 A1, EP 0471 177 B1, US2011/0195086 A1. At the conclusion of the conjugation reaction, unreacted aldehydes are capped by addition of a strong reducing agent, such as sodium borohydride.

In one embodiment, the chemical activation of the polysaccharides and subsequent conjugation to the mDT are achieved by means described in U.S. Pat. Nos. 4,365,170, 4,673,574 and 4,902,506. Briefly, the polysaccharide is reacted with a periodate-based oxidizing agent such as sodium periodate, potassium periodate, or periodic acid resulting in random oxidative cleavage of vicinal hydroxyl groups to generate reactive aldehyde groups. Direct aminative coupling of the oxidized polysaccharide to primary amine groups on the mDT (mainly lysine residues) may then be accomplished by reductive amination. For example, conjugation is carried out by reacting a mixture of the activated polysaccharide and mDT with a reducing agent such as sodium cyanoborohydride in the presence of nickel. The conjugation reaction may be carried out in aqueous solution or in an organic solvent such as dimethyl sulfoxide (DMSO). See, e.g., US2015/0231270 A1, EP 0471 177 B1, US2011/0195086 A1. At the conclusion of the conjugation reaction, unreacted aldehydes are optionally reduced by addition of a strong reducing agent, such as sodium borohydride.

In one embodiment, prior to formulation, each pneumococcal capsular polysaccharide is individually purified from S. pneumoniae, activated to form reactive aldehydes, and then covalently conjugated to a mDT using reductive amination with sodium cyanoboroydride in the presence of nickel. Nickel forms complexes with residual, interfering cyanide from the sodium cyanoborohydride reducing agent used for reductive amination. Thus, nickel may be used in the methods herein for greater conjugation reaction efficiency and to aid in free cyanide removal.

Transition metals are known form stable complexes with cyanide and are known to improve reductive methylation of protein amino groups and formaldehyde with sodium cyanoborohydride. See Gidley et al., *Biochem J.* 1982, 203: 331-334; Jentoft et al. *Anal Biochem.* 1980, 106: 186-190. However, Applicants surprisingly found that by complexing residual, interfering cyanide, the addition of nickel increases the consumption of protein during the conjugation of and leads to formation of larger, potentially more immunogenic conjugates.

Variability in free cyanide levels in commercial sodium cyanoborohydride reagent lots may lead to inconsistent conjugation performance, resulting in variable conjugate attributes, including molecular mass and polysaccharide-to-protein ratio. The addition of nickel to the conjugation reaction reduces the level of free cyanide and thus improves the degree of lot-to-lot conjugate consistency.

In another embodiment, the conjugation method may employ activation of polysaccharide with 1-cyano-4-dimethylamino pyridinium tetrafluoroborate (CDAP) to form a cyanate ester. The activated saccharide may be coupled directly to an amino group on the mDT.

In an alternative embodiment, a reactive homobifunctional or heterobifunctional group may be introduced on the activated polysaccharide by reacting the cyanate ester with any of several available modalities. For example, cystamine or cysteamine may be used to prepare a thiolated polysaccharide which could be coupled to the mDT via a thioether linkage obtained after reaction with a maleimide-activated mDT (for example using GMBS) or a haloacetylated mDT (for example using iodoacetimide [e.g. ethyl iodoacetimide HCl] or N-succinimidyl bromoacetate or SIAB, or SIA, or SBAP). Such conjugates are described in International Patent Application Publication Nos. WO 93/15760, WO 95/08348 and WO 96/29094; and Chu et al., 1983, Infect. Immunity 40:245-256.

Other suitable conjugation methods use carbodiimides, hydrazides, active esters, norborane, p-nitrobenzoic acid, N-hydroxysuccinimide, S-NHS, EDC, TSTU. Many are described in International Patent Application Publication No. WO98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with mDT to form a carbamate linkage. This chemistry consists of reduction of the anomeric terminus of a carbohydrate to form a primary hydroxyl group followed by reaction of the primary hydroxyl with CDI to form a carbamate intermediate and subsequent coupling to mDT amino groups. The reaction may require optional protection/deprotection of other primary hydroxyl groups on the saccharide.

The following examples are intended to promote a further understanding of the present invention.

Example 1

Preparation of *S. Pneumoniae* Capsular Polysaccharides 6A, 6B, 7F, 18C, 19A, 19F, and 23F.

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP0497524. Isolates of pneumococcal subtypes are available from the American Type Culture Collection (Manassas, Va.). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the *S. pneumococcus* serotypes present are obtained from the Merck Culture Collection (Rahway, N.J.) in a frozen vial. A thawed seed culture is transferred to the seed fermenter containing a pre-sterilized growth media appropriate for *S. pneumoniae*. The culture is grown in the seed fermenter with temperature and pH control. The entire volume of the seed fermenter is transferred to a production fermenter containing pre-sterilized growth media. The production fermentation is the final cell growth stage of the process. Temperature, pH, and the agitation rate are controlled.

The fermentation process is terminated via the addition of an inactivating agent. After inactivation, the solution is transferred to the inactivation tank where it is held at controlled temperature and agitation. Cell debris is removed using a combination of centrifugation and filtration. The solution is ultrafiltered and diafiltered. The solution is then subjected to solvent-based fractionations that remove impurities and recover polysaccharide.

Example 2

Polysaccharide size reduction and activation is performed as follows.

About 6 g of purified pneumococcal capsular polysaccharide (Ps) powder is dissolved in water for injection (WFI) to a target concentration of approximately 4 g/L at room temperature. The solution is then 0.45-micron filtered to reduce bioburden. The Ps concentration of the filtered Ps solution is determined by HPSEC UV-MALS-RI.

For all serotypes disclosed herein except for serotypes 18C and 19A, the solution comprising the Ps is diluted to approximately 2.5 g/L and then homogenized to reduce the molecular mass of the Ps using a GEA-Niro Soavi Panda 2K homogenizer. Homogenizer pressure and the number of passes through the homogenizer are controlled to serotype-specific values (Table 1). Temperature is controlled during homogenization using a chilled water supply to a heat exchanger at the outlet of the homogenizer.

TABLE 1

Serotype-Specific Homogenization Parameters

| Serotype | MBC Lot Number | Homogenizer Pressure (bar) | Number of Passes |
|---|---|---|---|
| 6A | Lot A | 200 | 5 |
| | Lot B | | |
| 6B | Lot A | 200 | 5 |
| | Lot B | | |
| 7F | Lot A | 150 | 7 |
| | Lot B | | |
| 18C | Lot A | Not applicable[1] | Not applicable[1] |
| | Lot B | | |
| 19A | Lot A | Not applicable[2] | Not applicable[2] |
| | Lot B | | |
| 19F | Lot A | 150 | 5 |
| | Lot B | | |
| 23F | Lot A | 400 | 5 |
| | Lot B | | |

[1] Acid hydrolysis is used to size reduce serotype 18C.
[2] Serotype 19A is not size-reduced due to its relatively low starting size.

TABLE 2

Serotype-Specific Activation Parameters

| Serotype | MBC Lot Number | Activation Temperature (° C.) | Sodium Acetate Concentration (mM) | pH of 2M Sodium Acetate Stock Buffer | Sodium Periodate Charge (meq) | Activation Reaction Time (hrs) |
|---|---|---|---|---|---|---|
| 6A | Lot A | 22 | 50 | 5.0 | 0.10 | 2 |
| | Lot B | | | | | |
| 6B | Lot A | 22 | 50 | 5.0 | 0.10 | 2 |
| | Lot B | | | | | |
| 7F | Lot A | 4 | 50 | 5.0 | 0.24 | 4 |
| | Lot B | | | | | |
| 18C | Lot A | 22 | 50 | 5.0 | 0.14 | 2 |
| | Lot B | | | | | |
| 19A | Lot A | 22 | 50 | 5.0 | 0.26 | 20 |
| | Lot B | | | | | |
| 19F | Lot A | 4 | 50 | 5.0 | 0.10 | 4 |
| | Lot B | | | | | |
| 23F | Lot A | 22 | 50 | 5.0 | 0.15 | 4 |
| | Lot B | | | | | |

Acid hydrolysis is used instead of homogenization to reduce the molecular mass of the serotype 18C Ps. The temperature of the filtered serotype 18C Ps solution is increased to approximately 96° C. for Lot A and 90° C. for Lot B. The solution is then adjusted with glacial acetic acid (17.4 M) to target a final concentration of 0.2 M and held for approximately 180 minutes for Lot A and 160 minutes for Lot B. 1.5 M potassium phosphate, pH 7.0 is added to a final concentration of 0.46 M to stop the acid hydrolysis by increasing the solution pH, and the solution is then cooled to room temperature.

Solutions comprising serotype 19A are not 0.45-micron filtered or size-reduced. Due to its relatively low starting size, size reduction is not required. Following dissolution, serotype 19A is 0.22-micron filtered as described in the next paragraph.

Each solution is then filtered using a 0.22-micron filter to reduce bioburden prior to the Ultrafiltration 1 step. The filtered Ps is concentrated to approximately 10 g/L using a 10 kDa NMWCO tangential flow ultrafiltration membrane and then diafiltered against 6 diavolumes of WFI at ambient temperature, generating the Ultrafiltration 1 process intermediate (UF1-FR). Serotype 18C used a 5 kDa NMWCO membrane instead of a 10 kDa NMWCO membrane to improve Ps recovery by retaining lower molecular weight Ps generated by acid hydrolysis. The Ps concentration of the UF1-FR is determined by HPSEC UV-MALS-RI. WFI is added to the UF1-FR to achieve a Ps concentration of approximately 10 g/L prior to Ps activation. 2 M sodium acetate buffer is then added to control the pH of the activation reaction step. The sodium acetate concentration and pH, and temperature during the Ps activation reaction are controlled to specific values for each serotype (Table 2).

The periodate activation is initiated by adding a 100 mM sodium metaperiodate solution to the solution on a basis of moles of periodate per mole of PnPs repeating unit (RU). During the activation, vicinal diols are oxidized to reactive aldehydes over a serotype-specific reaction time. This reaction generated the activated product (AP) process intermediate. The amount of sodium metaperiodate charged and the reaction time are controlled to specific values for each serotype (Table 2).

Following Ps activation, the solution is diafiltered against 6 diavolumes of 10 mM potassium phosphate, pH 6.4, followed by an additional 6 diavolumes of WFI using a 10 kDa NMWCO tangential flow ultrafiltration membrane at 2-8° C. Serotype 18C used a 5 kDa NMWCO membrane instead of a 10 kDa NMWCO membrane to improve Ps recovery by retaining lower molecular weight Ps generated by acid hydrolysis. The solution is then concentrated, generating the Ultrafiltration 2 process intermediate (UF2-FR). The Ps concentration of the UF2-FR is determined by HPSEC UV-MALS-RI. The extent of activation is determined by derivatizing a UF2-FR sample with thiosemicarbazide, then detecting thiosemicarbazone by HPSEC with UV detection.

Example 3

Preparation of $CRM_{197}$ may be performed as follows.

Frozen, purified $CRM_{197}$, obtained through expression in *Pseudomonas fluorescens* as previously described (See International Patent Application Publication No. WO 2012/173876), is diafiltered against 10 diavolumes of 2 mM phosphate, pH 7.2 buffer using a 5 kDa NMWCO tangential flow ultrafiltration membrane and 0.22-micron filtered. In particular embodiments, 5 mM potassium phosphate, pH 6.4 (5 mM sodium phosphate, pH 7.0 is used when intended to be conjugated to serotype 18C). The diafiltered solution is diluted in water with sucrose for a final concentration of between 1.0 and 5.3% (w/v) and lyophilized to produce dried $CRM_{197}$ having a final moisture content of 6% or less. Table 3 below provides representative sucrose concentrations for CRM197 for conjugation against particular serotype polysaccharides.

Example 4

Lyophilization of Polysaccharide (Ps) and $CRM_{197}$ (Pr) is as follows.

Prior to lyophilization, the $CRM_{197}$ and Ps solutions are diluted as described below.

In some embodiments, the $CRM_{197}$ solution is diluted to a protein concentration of 6.0 mg/mL using WFI, 5 mM sodium phosphate, pH 6.4 (pH 7.0 for serotype 18C), and a freshly prepared 30% (w/v) sucrose solution in WFI. The UF2-FR Ps solution is diluted to a Ps concentration of 6.0 mg/mL using WFI and a freshly prepared 30% w/v sucrose solution in WFI.

In some embodiments, the CRM197 solution is diluted to a protein concentration of 6.0 mg/mL using WFI, 2 mM sodium phosphate, pH 7.2, and a freshly prepared 50% (w/v) sucrose solution in WFI. The UF2-FR Ps solution is diluted to a Ps concentration of 6.0 mg/mL using WFI and a freshly prepared 50% (w/v) sucrose solution in WFI.

Serotype-specific sucrose and phosphate concentrations are used (See for example, Table 3). The diluted $CRM_{197}$ and UF2-FR solutions are lyophilized using a Virtis Genesis Freeze Dryer.

TABLE 3

Serotype-Specific Lyophilization Parameters

| Serotype | MBC Lot Number | Sucrose Concentration in CRM197 Solution Prior to Lyophilization (% w/v) | Sodium Phosphate Concentration in CRM197 Solution Prior to Lyophilization (mM) | Sucrose Concentration in UF2-FR Ps Solution Prior to Lyophilization (% w/v) |
|---|---|---|---|---|
| 6A | Lot A | 4.0 | 3.8 | 4.0 |
|  | Lot B | 1.0 | 1.25 | 5.0 |
| 6B | Lot A | 1.0 | 2.3 | 3.5 |
|  | Lot B |  | 1.25 | 5.0 |
| 7F | Lot A | 5.3 | 2.4 | 5.3 |
|  | Lot B | 1.0 | 1.25 | 5.0 |
| 18C | Lot A | 2.4 | 2.8 | 4.0 |
|  | Lot B | 1.0 | 1.25 | 5.0 |
| 19A | Lot A | 1.0 | 1.6 | 3.0 |
|  | Lot B |  | 1.25 | 5.0 |
| 19F | Lot A | 1.0 | 2.3 | 5.0 |
|  | Lot B |  | 1.25 |  |
| 23F | Lot A | 3.0 | 1.7 | 3.0 |
|  | Lot B | 1.0 | 1.25 | 5.0 |

Example 5

This example shows that reconstitution time of $CRM_{197}$ in DMSO affects the secondary structure as measured by Fourier Transfer Infrared Spectroscopy (FTIR).

Lyophylized $CRM_{197}$ that had been lyophilized at 6 mg/mL, 5% (w/v) sucrose, 1.25 mM sodium phosphate, pH 7.2 is reconstituted in DMSO (anhydrous DMSO from Sigma-Aldrich, 27655-100 mL) to a final concentration of 10 mg/mL using either slow (eight minutes) or fast reconstitution (two minutes) and then mixed to produce homogenous solutions. Reconstitution is carried out by adding the appropriate volume of DMSO every 30 seconds until the time point is reached. FTIR spectra are collected with a BioTools PROTA-3S at controlled temperature (25° C.) using transmission mode with 50 mm $CaF_2$ windows. Fifty scans may be collected with a resolution of 4 cm$^{-1}$, averaged, buffer subtracted and water vapor corrected.

Lyophilized $CRM_{197}$ reconstituted in DMSO with fast addition (two minutes) shows the expected free carbonyl amide I peak at 1660 cm$^{-1}$, which demonstrates complete unfolding of $CRM_{197}$ in DMSO (FIG. 1). When $CRM_{197}$ is reconstituted in DMSO with slow addition time (eight minutes), a second peak (1626 cm$^{-1}$) in the amide I region is present. This second peak is attributed to intermolecular beta-sheet formation.

Example 6

This example shows that $CRM_{197}$ reconstituted at an intermediate reconstitution time (four minutes) and held for up to 300 minutes leads to an increase in the proportion of intermolecular beta-sheet as the hold time increases.

Lyophylized $CRM_{197}$ that had been lyophilized at 6 mg/mL, 5% (w/v) sucrose, 1.25 mM sodium phosphate, pH 7.2 is reconstituted in DMSO (anhydrous DMSO from Sigma-Aldrich, 27655-100 mL) to a final concentration of 10 mg/mL over the course of 4 minutes. Reconstitution is carried out by adding the appropriate volume of DMSO every 30 seconds until the time point is reached. After the initial time point is collected (T0), the sample is held in the FTIR and further time points are collected (30, 60, 120, 180, 240, 300 minutes). FTIR spectra are collected with a BioTools PROTA-3S at controlled temperature (25° C.) using transmission mode with 50 mm $CaF_2$ windows. Fifty scans may be collected with a resolution of 4 cm$^{-1}$, averaged, buffer subtracted and water vapor corrected.

Figure 2:
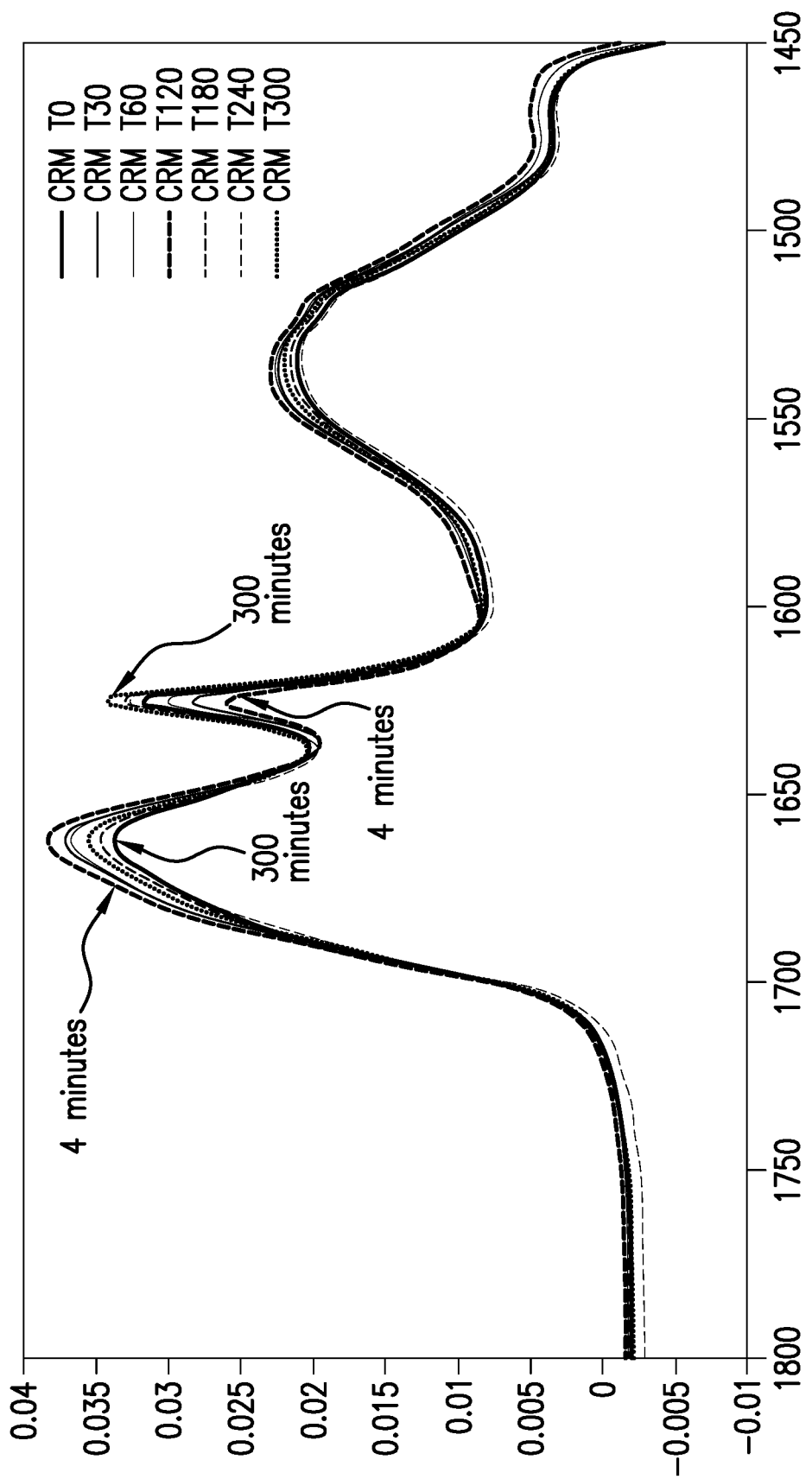
FIG. 2 shows FTIR spectra of $CRM_{197}$ with intermediate reconstitution in anhydrous DMSO (four minutes) followed by increasing hold time (30 minutes; 60 minutes; 120 minutes; 180 minutes; 240 minutes; 300 minutes).

Reconstitution of $CRM_{197}$ in DMSO at intermediate time (4 minutes) leads to protein aggregation, as demonstrated by the presence of an intermolecular beta-sheet amide I peak (FIG. 2). Increased hold time, up to 300 minutes leads to a proportionally increasing amount of intermolecular beta-sheet and decreasing amounts of free carbonyl amide I peak (FIG. 2).

Example 7

This example shows formation of intermolecular beta-sheet is concentration dependent.

Lyophylized $CRM_{197}$ that had been lyophilized at 6 mg/mL, 5% (w/v) sucrose, 1.25 mM sodium phosphate, pH 7.2 is reconstituted in DMSO (anhydrous DMSO may be from Sigma-Aldrich, 27655-100 mL) to a final concentration of 10, 30, or 50 mg/mL over the course of two minutes. Reconstitution is carried out by adding the appropriate volume of DMSO every 30 seconds until the time point is reached.

FTIR spectra are collected with a BioTools PROTA-3 S at controlled temperature (25° C.) using transmission mode with 50 mm $CaF_2$ windows. Fifty scans may be collected with a resolution of 4 cm$^{-1}$, averaged, buffer subtracted and water vapor corrected. Dynamic light scattering (DLS) measurements are collected with a Malvern Zetasizer ZS at controlled temperature (25° C.) at the prepared concentration using a viscosity of 1.996 cP.

When $CRM_{197}$ is fast reconstituted (FIG. 3, two minutes) at 10 mg/mL, there is no evidence of intermolecular beta-sheet formation, confirming earlier observations (FIG. 1). At higher concentrations (30 mg/mL, 50 mg/mL), intermolecular beta-sheet is formed, even at fast reconstitution times (two minutes). This supports the hypothesis that the increased $CRM_{197}$ concentration present during slow reconstitution is one of the causes of the formation of intermolecular beta-sheets. Also supporting this concentration hypothesis are the DLS data, which demonstrates an increase in the proportion of larger particles in $CRM_{197}$ reconstituted at higher concentrations (FIG. 4B) as compared with lower concentrations (FIG. 4A), consistent with protein aggregation.

Example 8

Increasing the concentration of water in the DMSO used for reconstituting the $CRM_{197}$ leads to increasing formation of intermolecular beta-sheets.

Lyophylized $CRM_{197}$ that had been lyophilized at 6 mg/mL, 5% (w/v) sucrose, 1.25 mM sodium phosphate, pH 7.2 is reconstituted in DMSO (anhydrous DMSO may be from Sigma-Aldrich, 27655-100 mL) to a final concentration of 10 mg/mL over the course of two minutes in DMSO/water at 95%, 97%, 99% (v/v) or anhydrous DMSO. Anhydrous DMSO may be Sigma-Aldrich D2438-50 mL. Reconstitution is carried out by adding the appropriate volume of DMSO every 30 seconds until the time point is reached. FTIR spectra are collected with a BioTools PROTA-3S at controlled temperature (25° C.) using transmission mode with 50 mm $CaF_2$ windows. 50 scans are collected with a resolution of 4 $cm^{-1}$, averaged, buffer subtracted and water vapor corrected.

Figure 3:
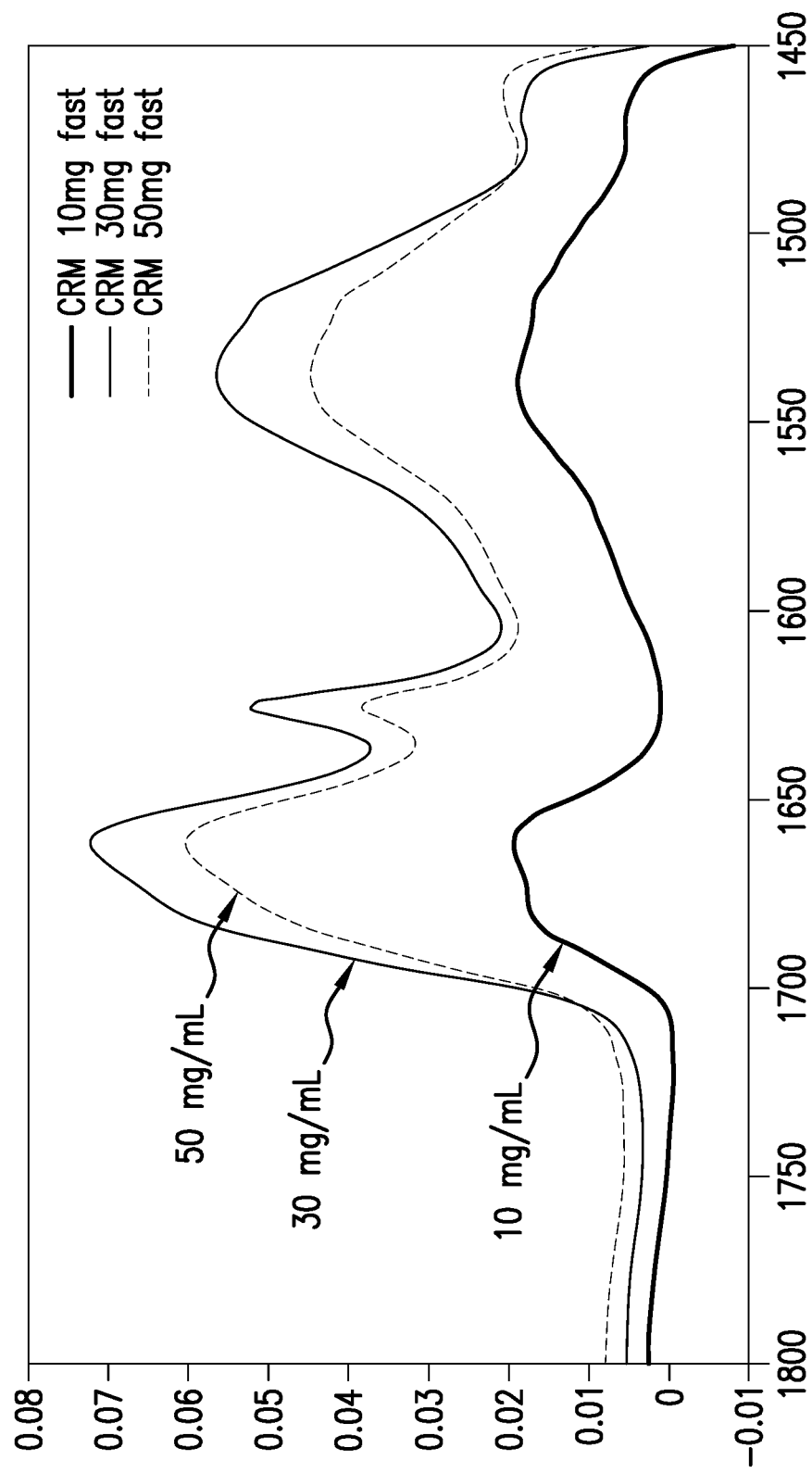
FIG. 3 shows FTIR spectra of $CRM_{197}$ with fast reconstitution in anhydrous DMSO (two minutes) at different concentrations (10 mg/mL; 30 mg/mL; 50 mg/mL).
Figure 4A:
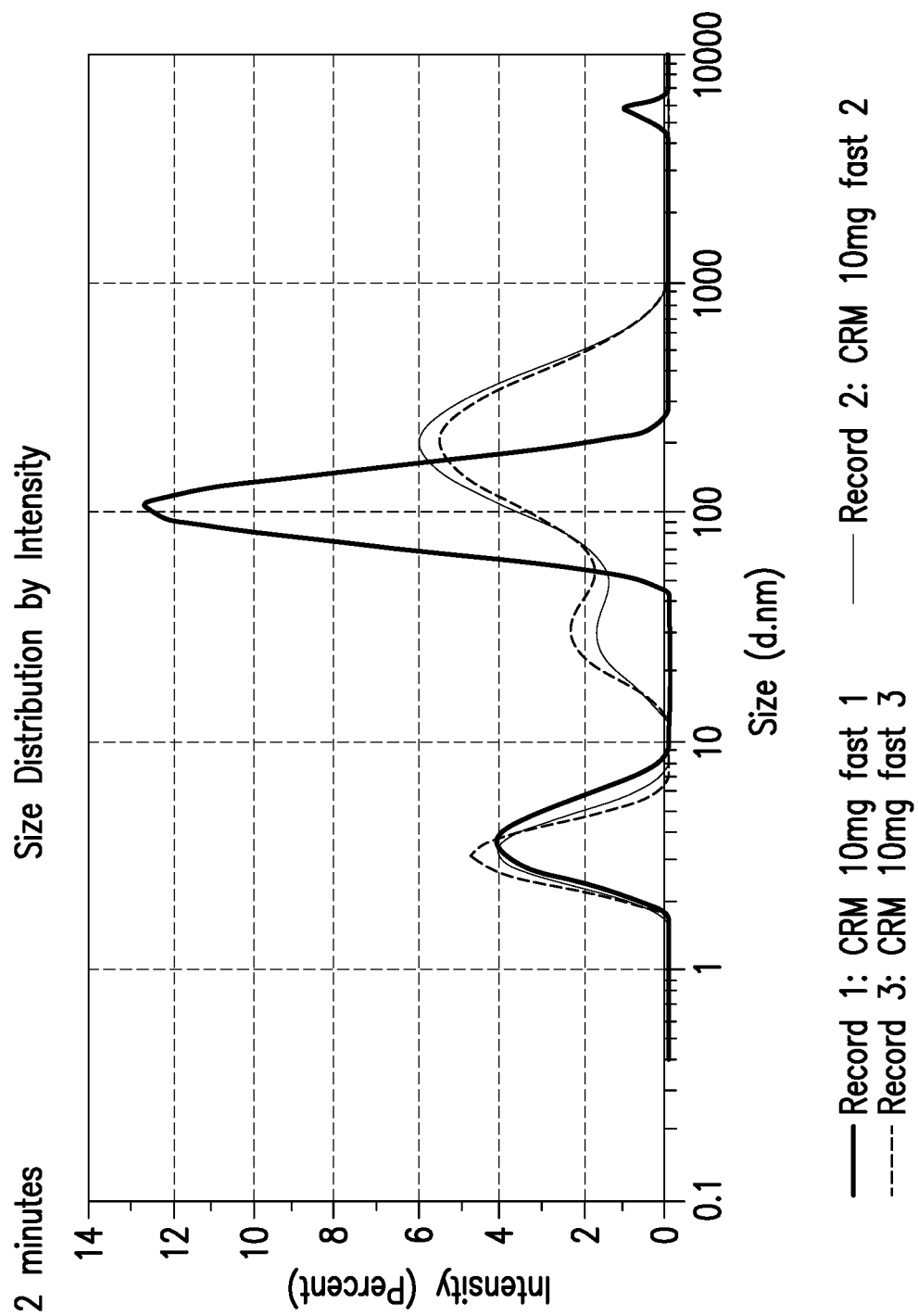
FIGS. 4A and 4B show Dynamic light scattering (DLS) profiles of $CRM_{197}$ with fast reconstitution (two minutes) in anhydrous DMSO at 10 mg/mL (FIG. 4A) and 30 mg/mL (FIG. 4B). Three measurements were collected for each sample (the three traces).
Figure 4B:
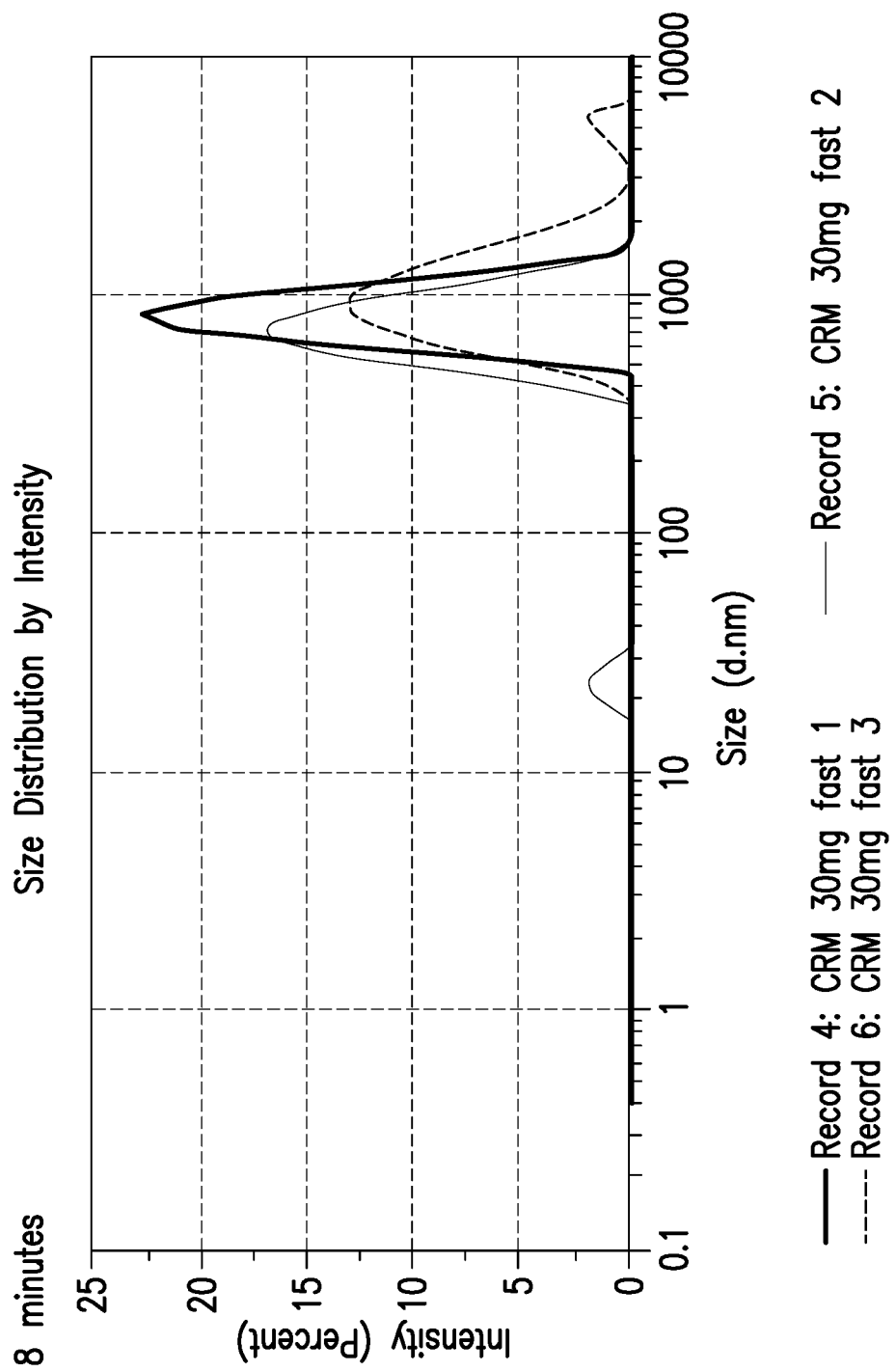

When $CRM_{197}$ is fast reconstituted at 10 mg/mL in anhydrous DMSO (FIG. 5), there is no evidence of intermolecular beta-sheet formation, confirming earlier observations (FIG. 1, FIG. 3). A very small amount of water (99% DMSO/water) shows a small shoulder of intermolecular beta-sheet, with the amount increasing with increased water (97%, 95% DMSO/water). This supports the hypothesis that increasing amounts of water in the reconstitution lead to increased amounts of intermolecular beta-sheet formation.

Example 9

Reducing the moisture level in lyophilized $CRM_{197}$ does not reduce the sensitivity to slow reconstitution.

$CRM_{197}$ is lyophilized in a way to reduce moisture present in the cake (longer dry cycle, lower fill volume) (about 6 mg/mL in 1% (w/v) sucrose with 1.25 mM phosphate, pH 7.2). The lyophilized $CMR_{197}$ is reconstituted to a final concentration of 10 mg/mL over the course of two or eight minutes in DMSO (e.g., anhydrous DMSO from Sigma-Aldrich D2438-50 mL). Reconstitution is carried out by adding the appropriate volume of DMSO every 30 seconds until the time point is reached. FTIR spectra are collected with a BioTools PROTA-3S at controlled temperature (25° C.) using transmission mode with 50 mm $CaF_2$ windows. Fifty scans are collected with a resolution of 4 $cm^{-1}$, averaged, buffer subtracted and water vapor corrected.

Figure 5:
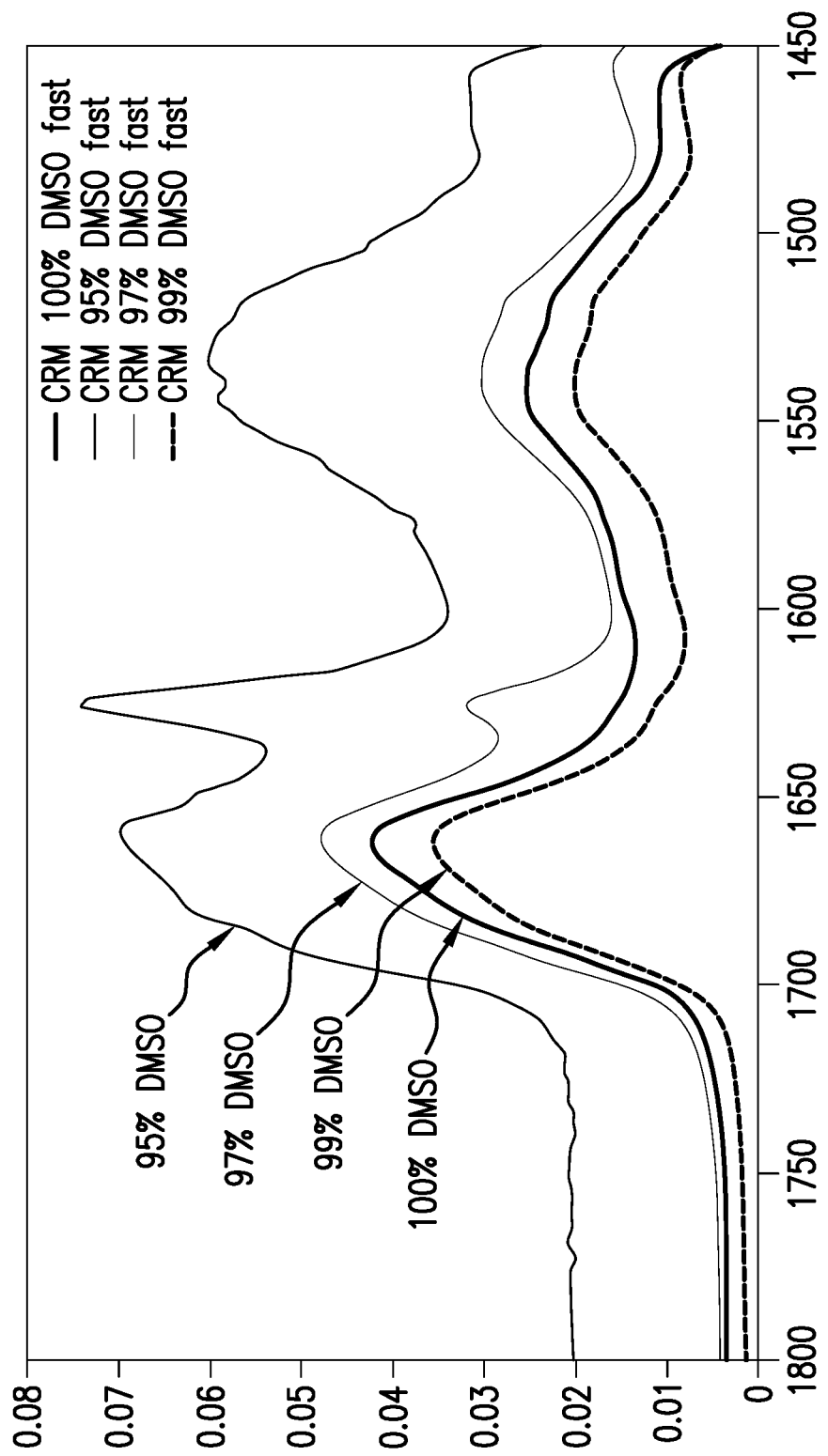
FIG. 5 shows FTIR spectra of $CRM_{197}$ with fast reconstitution in DMSO (two minutes) with different levels of water (anhydrous DMSO; 99% DMSO/water; 97% DMSO/water; 95% DMSO/water).
Figure 6:
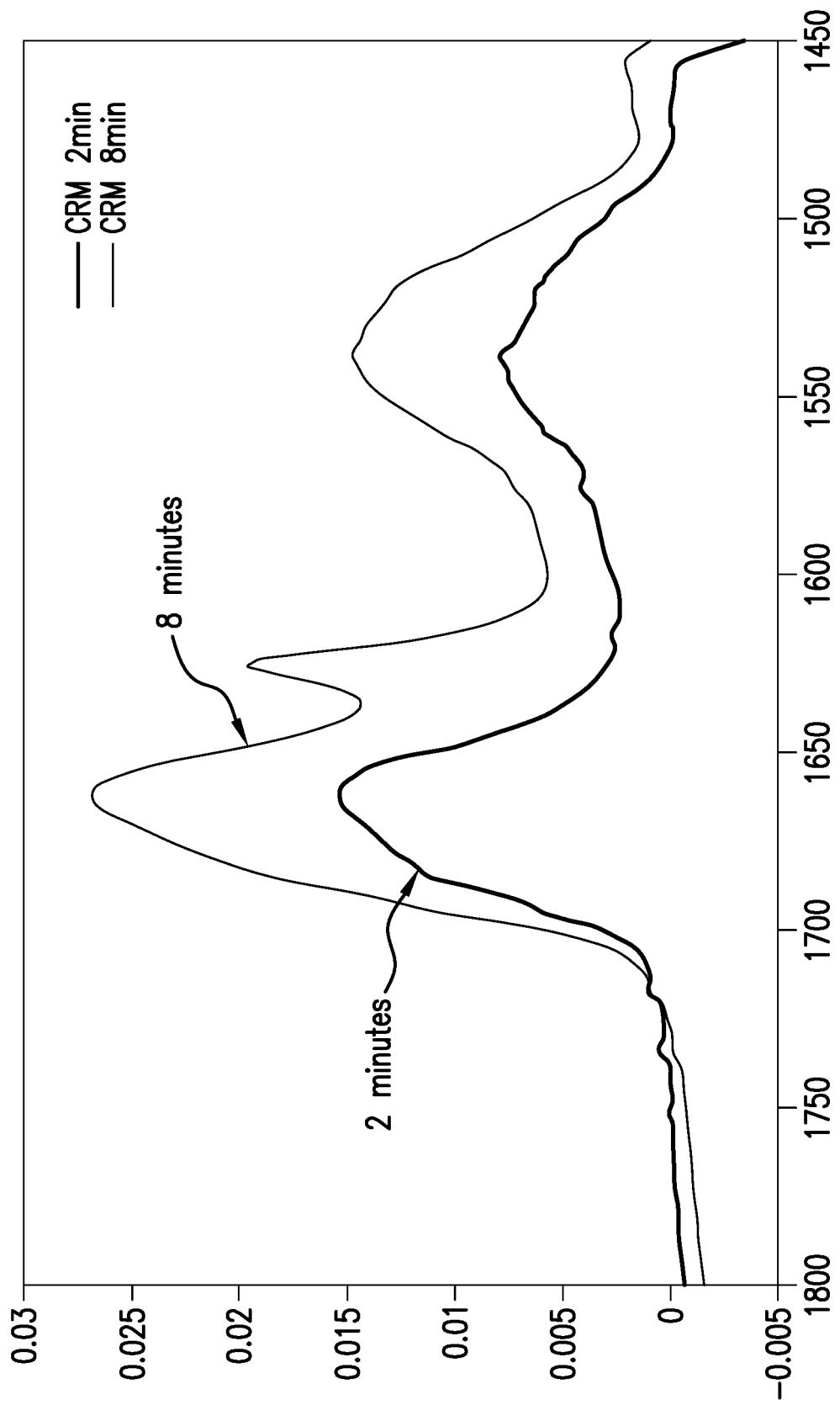
FIG. 6 shows FTIR spectra of extra dry lyophilized $CRM_{197}$ with fast (two minutes) vs. slow (eight minutes) reconstitution in anhydrous DMSO.
Figure 7:
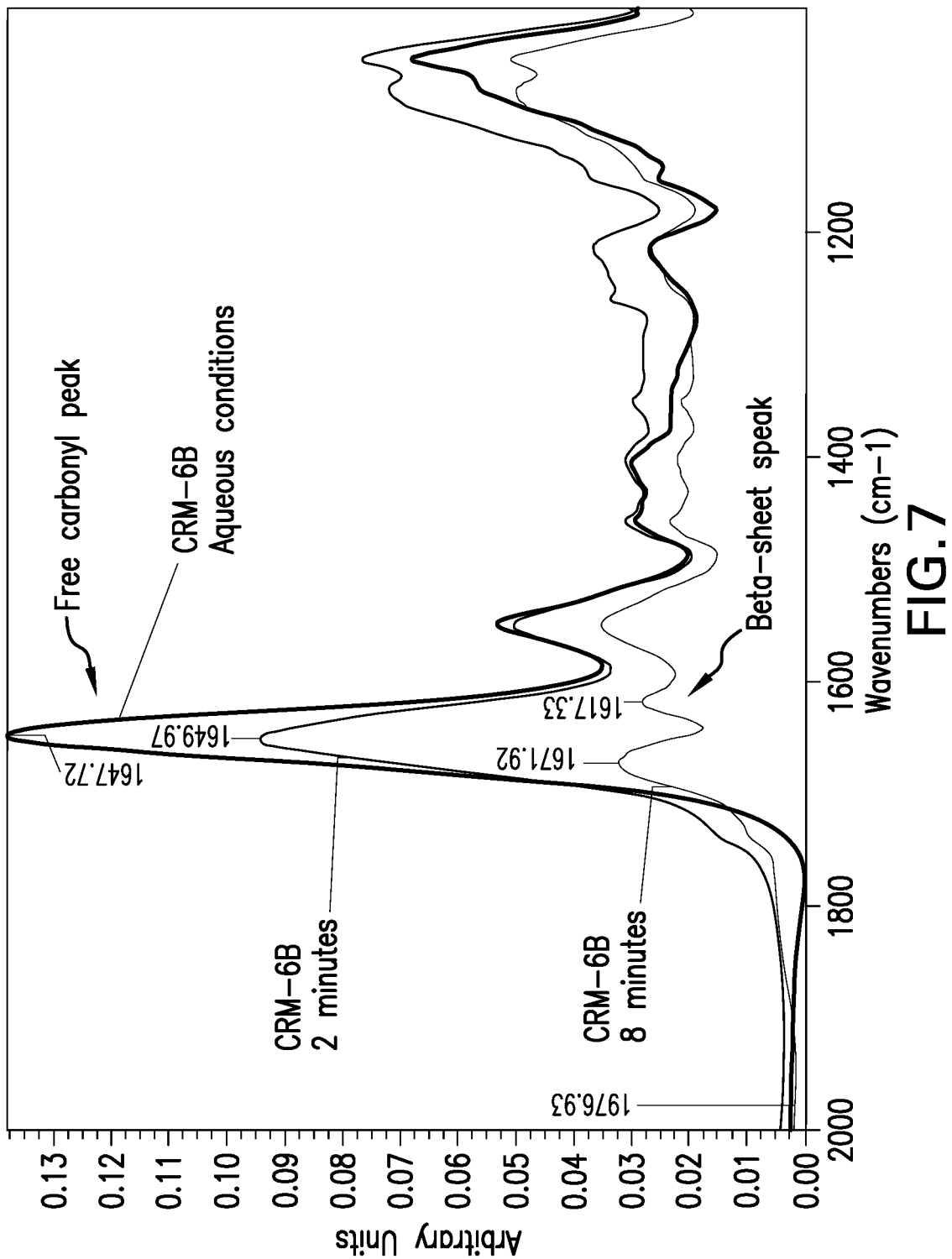
FIG. 7 shows FTIR spectra of $CRM_{197}$: polysaccharide serotype 6B ($CRM_{197}$-6B) conjugates where $CRM_{197}$ had been reconstituted fast (two minutes), or slow (eight minute) prior to polysaccharide 6B conjugation. Also shown is $CRM_{197}$ conjugated to polysaccharide 6B under aqueous conditions.

Increased water in the DMSO reconstitution of $CRM_{197}$ leads to an increase in the proportion of intermolecular beta-sheet formation (FIG. 5). $CRM_{197}$ that has been lyophilized in a manner to reduce the moisture content are reconstituted in anhydrous DMSO at two different rates, fast (two minutes) and slow (eight minutes). The decreased water content of the lyophilized $CRM_{197}$ does not decrease the sensitivity of the $CRM_{197}$ to the formation of intermolecular beta-sheets over reconstitution time (FIG. 6).

Example 11

The lyophilized Ps and $CRM_{197}$ (Pr) are re-dissolved at ambient temperature using equal volumes of anhydrous DMSO to make Ps and Pr homogenous solutions. The $CRM_{197}$ is re-dissolved at a fast rate of 2 minutes. In some embodiments, 500 mM sodium phosphate, pH 7.2 buffer is spiked into the DMSO-redissolved protein solution to a final concentration of 1.0 mM sodium phosphate. Following re-dissolution in DMSO, the Ps and $CRM_{197}$ solutions are combined as described above targeting a serotype-specific final Ps concentration and Ps:$CRM_{197}$ ratio (Table 4).

A solution of sodium cyanoborohydride in WFI is prepared, and 1.0 meq of sodium cyanoborohydride (1.0 mole of sodium cyanoborohydride per mole of Ps repeating unit) is added to the solution. The molarity of the sodium cyanoborohydride solution (Table 5) is based on the target of approximately 0.5% total water content of the solution during conjugation. The solution is allowed to react at serotype-specific temperature for a serotype-specific duration (Table 5), generating the Conjugated Product intermediate (CP).

A solution of sodium borohydride in WFI is prepared, and 2.0 meq of sodium borohydride (relative to Ps repeating units) is added to the solution. The molarity of the sodium borohydride solution (Table 5) is based on the target of approximately 1.0% total water content in the solution after borohydride addition. The solution is allowed to react for 2-3 hours at ambient temperature, generating the Conjugate Product Quenched intermediate (CPQ).

TABLE 4

Serotype-Specific DMSO Conjugation Parameters

| Serotype | MBC Lot Number | Ps Conc. during Conj. (g/L) | Ps:CRM197 Mass Ratio during Conjugation (w/w) | Conj. Temp. (° C.) | Sodium Cyano-borohydride Solution Conc. (mM) | Conj. Reaction Time (hr) | Sodium Borohydride Solution Conc. (mM) |
|---|---|---|---|---|---|---|---|
| 6A | Lot A | 1.1 | 1.4 | 23.0 | 321 | 48 | 643 |
|    | Lot B | 1.5 | 1.4 | 22.0 | 493 | 15 | 377 |
| 6B | Lot A | 1.6 | 1.35 | 18.5 | 467 | 3.5 | 935 |
|    | Lot B | 1.85 | 1.35 | 22.0 | 591 | 3 | 1081 |
| 7F | Lot A | 1.5 | 2.0 | 23.0 | 253 | 4 | 506 |
|    | Lot B | 2.6 | 1.5 | 22.0 | 465 | 4 | 878 |
| 18C | Lot A | 3.0 | 1.5 | 23.0 | 632 | 1 | 1265 |
|     | Lot B | 3.1 | 1.5 | 22.0 | 672 | 2 | 1307 |
| 19A | Lot A | 3.0 | 1.3 | 18.5 | 1014 | 1.5 | 2029 |
|     | Lot B | 3.8 | 1.33 | 22.0 | 1285 | 1.5 | 2570 |
| 19F | Lot A | 1.6 | 1.2 | 18.5 | 541 | 9 | 1082 |
|     | Lot B | 2.0 | 1.2 | 22.0 | 720 | 8 | 1353 |
| 23F | Lot A | 2.25 | 1.25 | 23.0 | 584 | 8 | 1168 |
|     | Lot B | 2.45 | 1.25 | 22.0 | 660 | 4 | 1272 |

The conjugation solutions are then diluted to 20% or less (v/v) anhydrous DMSO by slowly adding the solution to 150 mM sodium chloride (150 mM sodium chloride with 0.025% w/v polysorbate 20 for conjugates in some embodiments). The solution temperature is maintained at less than 15° C. during the dilution step. After about one hour, 1.5 M potassium phosphate, pH 6.0, is added to the solution to a final concentration of 25 mM potassium phosphate. Conjugation performance is assessed by overall Ps and $CRM_{197}$ consumption, conjugate Ps to $CRM_{197}$ ratio, and conjugate molecular weight.

The conjugation solutions are concentrated to approximately 2.5 g/L and diafiltered against 10 diavolumes of 150 mM sodium chloride or 25 mM potassium phosphate in 150 mM sodium chloride at 2-8° C. using a 30 kDa NMWCO tangential flow ultrafiltration membrane. This generated the Ultrafiltration 3 process intermediate (UF3-FR). The Ps concentration of the UF3-FR is determined by HPSEC UV-MALS-RI.

For 19F in some embodiments, the UF3-FR is 0.22-micron filtered and subsequently incubated at 22° C. for approximately 120 hours.

The UF3-FR solutions are then processed in the Ultrafiltration 4 step. During the Ultrafiltration 4 step in some embodiments, the solutions are concentrated to a Ps concentration of approximately 2.5 g/L and diafiltered against 20 diavolumes of 10 mM L-histidine in 150 mM sodium chloride, pH 7.0 at 2-8° C. using a 300 kDa NMWCO Biomax PES tangential flow ultrafiltration membrane. Serotype 7F used a 100 kDa NMWCO membrane for the Ultrafiltration 4 step. For serotype 6A, 6B, and 18C, the UF3-FR solutions are concentrated to approximately 3.5 g/L and diafiltered against 10 mM L-histidine in 150 mM sodium chloride, 0.03% w/v PS-20, pH 7.0 at 2-8° C. using a 300 kDa NMWCO Biomax PES tangential flow ultrafiltration membrane. In some embodiments, serotype 7F, 19A, 19F and 23F UF3-FR solutions are concentrated to approximately 2.0 g/L and diafiltered against 10 mM L-histidine in 150 mM sodium chloride, 0.015% w/v PS-20, pH 7.0 at 2-8° C. using a 300 kDa NMWCO UltraCel, regenerated cellulose, tangential flow ultrafiltration membrane. This generated the Ultrafiltration 4 process intermediate (UF4-FR). The Ps concentration of the UF4-FR is determined by HPSEC UV-MALS-RI.

The UF4-FR is 0.22-micron filtered through a PVDF filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, pH 7.0. This generated the Monovalent Bulk Conjugate intermediate (MBC). The MBC is dispensed into aliquots and frozen at −60° C. to −80° C.

The UF4-FR for serotype 6A, 6B, and 18C is 0.5/0.2-micron filtered through a dual-membrane PES filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, 0.03% w/v PS-20, pH 7.0. This generated the Monovalent Bulk Conjugate intermediate (MBC). The MBC is dispensed into aliquots and frozen at −60° C. to −80° C.

The UF4-FR for serotype 7F, 19A, 19F, and 23F are 0.22-micron filtered through a PVDF filter. The Ps concentration of the filtrate is determined by HPSEC UV-MALS-RI. If the Ps concentration of the filtrate is greater than 1.0 g/L, the filtrate is then diluted to a Ps concentration of 1.0 g/L with additional 10 mM L-histidine in 150 mM sodium chloride, 0.015% w/v PS-20, pH 7.0.

This generated the Monovalent Bulk Conjugate intermediate (MBC). The MBC is dispensed into aliquots and frozen at −60° C. to −80° C.

Example 12

Intermolecular beta-sheets are present after conjugation when $CRM_{197}$ is reconstituted in anhydrous DMSO slowly (eight minutes) and is subsequently conjugated to 6B polysaccharide.

$CRM_{197}$ is reconstituted in DMSO fast (two minutes) or slow (eight minutes) and is subsequently conjugated to 6B polysaccharide as discussed previously, purified as discussed previously, and diafiltered to a concentration of about 1 mg/mL in (10 mM Histidine, 150 mM NaCl pH7). Samples are then concentrated with Amicon Ultra 11K MWCO filters to enable FTIR measurement. FTIR spectra are collected with a BioTools PROTA-3 S at controlled temperature (25° C.) using transmission mode with 50 mm $CaF_2$ windows. Fifty scans are collected with a resolution of 4 $cm^{-1}$, averaged, buffer subtracted and water vapor corrected. Data are subsequently analyzed using Omic software (ThermoFisher).

$CRM_{197}$-6B conjugate that has been made with $CRM_{197}$ that had been reconstituted slowly in DMSO (FIG. 7) shows evidence of intermolecular beta-sheet formation, demonstrating that $CRM_{197}$ aggregation is present even after reconstitution. $CRM_{197}$-6B conjugate that has been made with $CRM_{197}$ reconstituted fast (FIG. 7) shows the expected free C=O amide and no apparent beta-sheet formation.

Example 13

This example shows a method for conjugation of Ps from serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, or 38 to $CRM_{197}$ (Pr) using reductive amination in anhydrous DMSO. The different serotype polysaccharides are individually conjugated to purified $CRM_{197}$ using a common process flow.

The dried $CRM_{197}$ prepared as previously described is reconstituted in anhydrous DMSO by fast addition of the anhydrous DMSO to the dried $CRM_{197}$ over two minutes and the Ps are each separately reconstituted in anhydrous DMSO to make Pr and Ps homogenous solutions. The Ps and Pr are each reconstituted in half the total conjugation reaction volume. Therefore, the Ps concentration after DMSO reconstitution is 2×Ps concentration during conjugation range of 2.2 to 7.6 g/L calculated from Table 4. Pr concentration after DMSO reconstitution is 2× (Ps concentration during conjugation/Ps:Pr ratio) range of 1.5 to 5.7 g/L. The Pr homogenous solution and the Ps homogenous solutions are then combined. Sodium cyanoborohydride (1 mole per mole of polysaccharide repeating unit) is then added to the mixture, and conjugation proceeded for a serotype-specific duration (1 to 48 hours) to achieve a targeted conjugate size.

Reduction with Sodium Borohydride

Sodium borohydride (2 mole per mole of polysaccharide repeating unit) is added following the conjugation reaction and the solution and incubated for 1 hour at 22° C. The solution is diluted into 150 mM sodium chloride, 0.025% (w/v) polysorbate 20, at approximately 4° C. Potassium phosphate buffer is then added to neutralize the pH. The solution is concentrated and diafiltered at approximately 4° C. against 150 mM sodium chloride using a 10 kDa NMWCO tangential flow ultrafiltration membrane.

Final Filtration and Product Storage

Each solution is then concentrated and diafiltered against 10 mM histidine in 150 mM sodium chloride, pH 7.0 at 4° C. using a 300 kDa NMWCO tangential flow ultrafiltration membrane. The retentate solution is 0.22-micron filtered.

Serotype 19F is incubated for approximately 5 days, diafiltered against 10 mM histidine in 150 mM sodium chloride, pH 7.0 at approximately 4° C. using a 300 kDa NMWCO tangential flow ultrafiltration membrane, and 0.22-micron filtered.

Serotype 18C is diafiltered against 10 mM histidine in 150 mM sodium chloride, pH 7.0 at approximately 4° C. using a 300 kDa NMWCO tangential flow ultrafiltration membrane, and 0.22-micron filtered.

The solutions are diluted with additional 10 mM histidine in 150 mM sodium chloride, pH 7.0 and dispensed into aliquots and frozen at <−60° C.

Example 14

This example shows formulation of a 15-valent Pneumococcal Conjugate Vaccine with different surfactants and stabilizers.

Pneumococcal polysaccharide-protein conjugates prepared as described above are used for the formulation of a 15-valent pneumococcal conjugate vaccine (PCV15) having serotypes 1, 3, 4, 5, 6A, 6B, 7F, 9V, 14, 18C, 19A, 19F, 22F, 23F, and 33F.

The formulations are prepared using pneumococcal polysaccharide-CRM$_{197}$ conjugates generated by reductive amination in anhydrous DMSO as discussed previously. The required volumes of bulk conjugates needed to obtain the target final concentration of individual serotype are calculated based on the solution volume and the bulk polysaccharide concentrations. The 15 conjugates are combined with the excipients selected from sodium chloride, L-histidine, pH 5.8 buffer with polysorbate (PS)-20, PS-80, or poloxamer (P)188.

The sterile formulated bulk is mixed gently during and following its combining with bulk Aluminum Phosphate Adjuvant (APA) with or without propylene glycol (PG) and polyethylene glycol 400 (PEG$_{400}$). Two concentrations of conjugates and APA are studied in the various formulations. One contained 8 μg/mL serotype 6B polysaccharide, 4 μg/mL polysaccharide for all other serotypes, and 250m/mL APA. The other contained 16 μg/mL serotype 6B polysaccharide, 8 μg/mL polysaccharide for all other serotypes, and 500m/mL APA. The formulated vaccines are stored at 2-8° C.

APA is an aqueous suspension of aluminum hydroxyphosphate. APA is manufactured by combining aluminum chloride and sodium phosphate in a 1:1 volumetric ratio to precipitate aluminum hydroxyphosphate. After the combining process, the material is size-reduced with a high-shear mixer to achieve a monodisperse particle size distribution. The product is then diafiltered against physiological saline and steam sterilized.

Example 15

In this example, 6B polysaccharide (Ps) and CRM$_{197}$ (Pr) prepared as discussed above are lyophilized discretely by REV to form dried cakes. The dried cakes are reconstituted in anhydrous DMSO and conjugated as discussed herein.

The target Ps:Pr ratio (w/w) is 0.9 to 1.5 and the target molecular weight (MW) of the conjugate is 1500 to 3500 kD. The target free Ps is 15% or less and a free lysine loss of greater the five mole/mole. The results are shown in Table 5. The REV dried material made according to the present invention has a conjugate MW within the target range, a Ps:Pr ratio within the target range, free Ps within the target range, and free lysine within the target range.

TABLE 5

| Sample ID | Conj MW [Mn] (kD) | Conj Ps:Pr (w/w) | Free Ps (%) | Free Pr-MEKC (%) | Lysine loss (mol/mol) |
|---|---|---|---|---|---|
| A | 3049 [1645] | 1.28 | N/A | <4 | 9.9 |
| B | 2426 [1257] | 1.25 | N/A | 4 | 9.0 |
| C | 2000-4000 [>700] | 0.7-1.1 | ≤10 | ≤5 | 8-12 |
| D | 3385 [1259] | 0.9 | 5 | 1 | 9.6 |
| E | 3187 [1649] | 1.2 | 1 | 2 | 9.9 |

Assay for Conjugate MW, Conjugate Mn, Conjugate Ps:Pr in Table 5

Molecular weight and concentration analysis of conjugates is determined using HPSEC/UV/MALS/RI assay. Conjugate samples are injected and separated by high performance size-exclusion chromatography (HPSEC). Detection is accomplished with ultraviolet (UV), multi-angle light scattering (MALS) and refractive index (RI) detectors in series. Protein concentration is calculated from UV$_{280}$ using an extinction coefficient. Polysaccharide concentration is deconvoluted from the RI signal (contributed by both protein and polysaccharide) using the do/dc factors which are the change in a solution's refractive index with a change in the solute concentration reported in mL/g. Average molecular weight of the samples are calculated by Astra software (Wyatt Technology Corporation, Santa Barbara, Calif.) using the measured concentration and light scattering information across the entire sample peak.

Assay for Lysine Loss in Table 5

Determination of lysine consumption in conjugated protein as a measure of the number of covalent attachments between polysaccharide and mDT is as follows.

The Waters AccQ-Tag amino acid analysis (AAA) is used to measure the extent of conjugation in conjugate samples. Samples are hydrolyzed using vapor phase acid hydrolysis in the Eldex workstation, to break the mDTs down into their component amino acids. The free amino acids are derivatized using 6-aminoquinolyl-N-hydroxysuccinimidyl carbamate (AQC). The derivatized samples are then analyzed using UPLC with UV detection on a C18 column. The average protein concentration is obtained using representative amino acids other than lysine. Lysine consumption during conjugation (i.e., lysine loss) is determined by the difference between the average measured amount of lysine in the conjugate and the expected amount of lysine in the starting protein.

Assay for Free Ps in Table 5

Free polysaccharide (polysaccharide that is not conjugated with CRM$_{197}$) is measured by first precipitating free protein and conjugates with deoxycholate (DOC) and hydrochloric acid. Precipitates are then filtered out and the filtrates are analyzed for free polysaccharide concentration by HPSEC/UV/MALS/RI. Free polysaccharide is calculated as a percentage of total polysaccharide measured by HPSEC/UV/MALS/RI.

Assay for Free Pr in Table 5

Free polysaccharide, polysaccharide-CRM197 conjugate, and free $CRM_{197}$ in conjugate samples are separated by capillary electrophoresis in micellar electrokinetic chromatography (MEKC) mode. Briefly, samples are mixed with MEKC running buffer containing 25 mM borate, 100 mM SDS, pH 9.3, and are separated in a preconditioned bare-fused 20 silica capillary. Separation is monitored at 200 nm and free CRM197 is quantified with a $CRM_{197}$ standard curve. Free protein results are reported as a percentage of total protein content determined by the HPSEC/UV/MALS/RI procedure.

Example 16

In this example, 23F polysaccharide (Ps) and $CRM_{197}$ (Pr) samples are prepared and lyophilized separately (discretely) according to the present invention or combined and lyophilized. The lyophilized samples are subsequently reconstituted in anhydrous DMSO and conjugated as discussed previously herein.

The target Ps:Pr ratio (w/w) is 0.9 to 1.5 and the target molecular weight (MW) of the conjugate is 1500 to 3500 kD. The results are shown in Table 6, which shows Ps and Pr on average were at the expected target for the separately lyophilized samples except for sample B2, which had a ratio of 2.4.

TABLE 6

| Sample | Ps (mg/mL) | Sucrose in Ps (w/v %) | Pr (mg/mL) | Sucrose in Pr (w/v %) | Drying cycle | Dissolution method | Conjugate MW | Conj Ps:Pr (w/w) |
|---|---|---|---|---|---|---|---|---|
| A2 | 6 | 3 | 6 | 3 | Lyo2 | Separate | 3828 | 1.3 |
|    |   |   |   |   |      | Combined | 5128 | 0.7 |
| B2 | 6 | 3 | 15 | 7.5 | Lyo2 | Separate | 1907 | 1.2 |
|    |   |   |    |     |      | Combined | 1903 | 2.1 |
| B2 | 8.4 | 4.2 | 8.4 | 4.2 | Lyo2 | Separate | 3154 | 2.4 |
|    |     |     |     |     |      | Combined | 1716 | 2.2 |
| C2 | 8.4 | 4.2 | 15 | 7.5 | Lyo2 | Separate | 2217 | 1.2 |
|    |     |     |    |     |      | Combined | 1457 | 1.9 |
| D2 | 8.4 | 4.2 | 15 | 7.5 | Lyo3 | Combined | 1998 | 0.7 |
| E2 | 8.4 | 4.2 | 15 | 7.5 | MDV1 | Combined | 272 | 0.7 |
| F2 | 8.4 | 4.2 | 15 | 7.5 | MDV2 | Combined | 2094 | 0.6 |

Example 17

This example shows the impact of anhydrous DMSO addition time to lyophilized $CRM_{197}$ (Pr) on conjugate size using 6A polysaccharide (Ps). As discussed previously, anhydrous DMSO was added to lyophilized Pr fast (two minutes) and slow (eight minutes), mixed, and then conjugated to activated Ps reconstituted in anhydrous DMSO.

Figure 9:
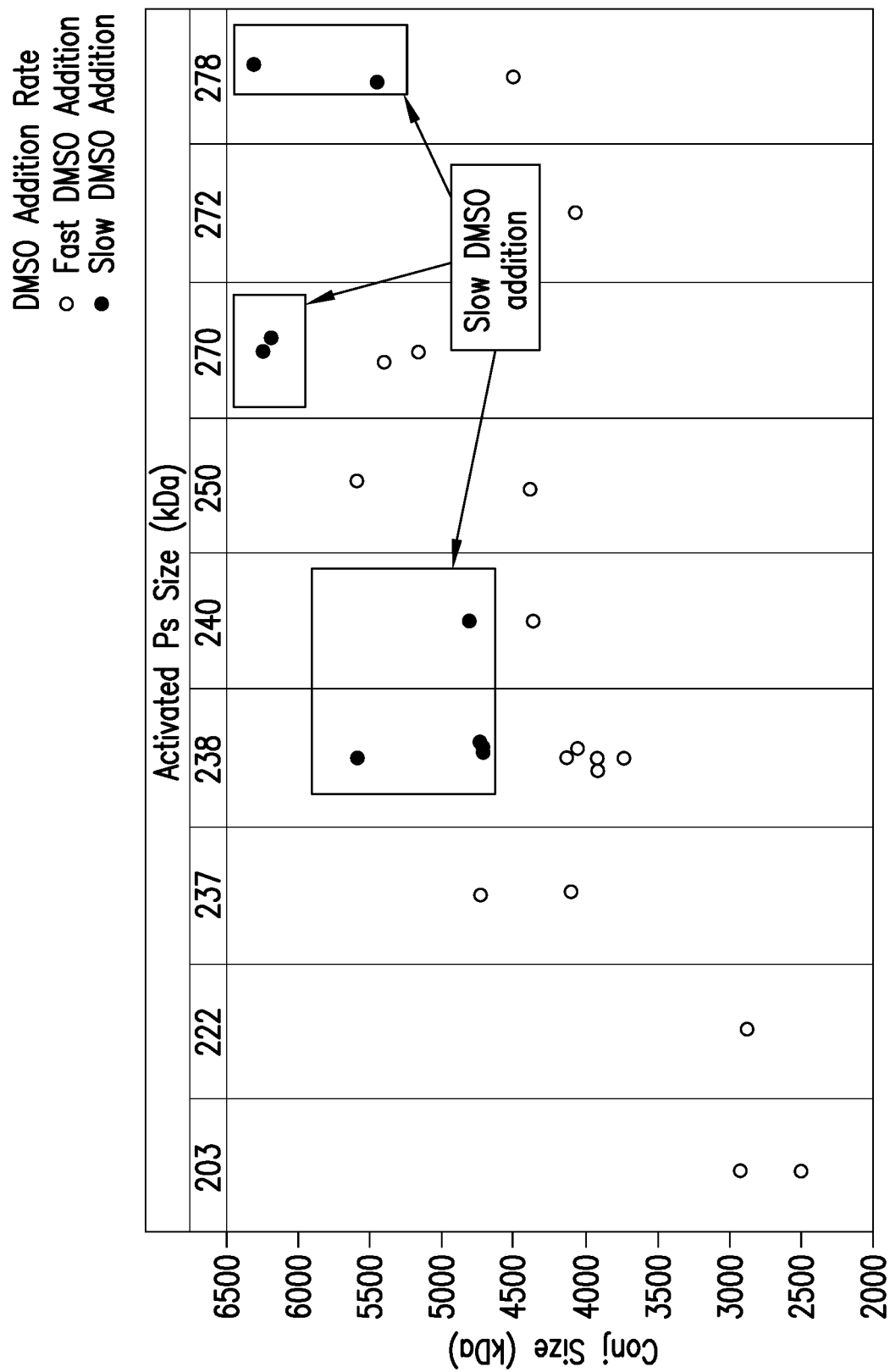
FIG. 9 shows the size of conjugate resulting from reactions using polysaccharides of increasing sizes. The graph shows that slow anhydrous DMSO addition results in an even larger conjugate from the same sized polysaccharide than fast addition of anhydrous DMSO.

FIG. 9 shows the size of conjugate resulting from conjugation reactions using polysaccharides of increasing sizes. The usual relationship is that the larger the polysaccharide (UF2 size) used for the conjugation reaction the larger the conjugate resulting therefrom. For each polysaccharide size, slow and fast anhydrous DMSO addition rates to the Pr after lyophilization were compared. The graph shows that slow anhydrous DMSO addition results in an even larger conjugate from the same sized polysaccharide than fast addition of anhydrous DMSO.

Example 5

This example shows development of lyophilizer conditions for producing polysaccharide (Ps) and CRM197 (Pr; CRM) lyospheres.

Discrete solutions of CRM and activated polysaccharides from serotypes 6A and 23F were prepared as described in Examples 3 and 4 and having Ps, CRM, and sucrose concentrations as shown in the tables in this example.

A modified Biomek FX pipetting robot (Cryomek) is used to dispense 50 μL aliquots of the solutions onto the flat freezing surface of the Cryomek. A shoveling mechanism may be used to dispense the beads onto a small cold container without causing any fractures. After completing the cycle for each different solution, the beads are transferred into an intermediate storage container and kept at −70° C. until sublimative drying in a lyophilizer or by microwave vacuum drying. For lyophilizer drying, beads are dispensed in a single layer into the drying trays. Cabinet pressure, shelf temperature and cycle time are set up. After drying the beads, the lyospheres are stored at 2-8° C. (See Example 5 for specific parameters)

The preliminary drying cycle (Lyo1) took 18 hours, as shown in Table 7.1. Residual moisture content of the lyospheres, determined by Karl Fisher titration, is shown on Table 7.2.

TABLE 7.1

Lyo1 Cycle Parameters

| Drying | Cabinet Pressure (mTorr) | Shelf Temperature (° C.) | Time (hours) |
|---|---|---|---|
| Primary | 30 | 15 | 18 |

TABLE 7.2

Karl Fisher Analysis for Lyospheres dried in Lyo1.

| Sample ID | Active material concentration (mg/mL) | Sucrose (w/v) | Residual moisture (%) |
|---|---|---|---|
| 6A Ps | 6 | 4 | 5.81 |
| CRM for 6A Ps | 6 | 4 | 6.16 |
| 23F Ps | 6 | 3 | 7.81 |
| CRM for 23F Ps | 6 | 3 | 10.4 |

The results show high moisture content in the lyospheres. In addition, lyospheres were very fragile and hydroscopic. Solids content was increased by increasing polysaccharide, protein, and sucrose concentrations, as shown in Table 8.2.

The drying cycle was modified (Lyo 2) by adding a secondary drying cycle and increasing the primary drying time, as shown in Table 8.1.

TABLE 8.1

Lyo2 Cycle Parameters

| Drying | Cabinet Pressure (mTorr) | Shelf Temperature (° C.) | Time (hours) |
|---|---|---|---|
| Primary | 30 | 15 | 40 |
| Secondary | 30 | 30 | 5 |

TABLE 8.2

Karl Fisher Analysis for Lyospheres Dried in Lyo2

| Sample ID | Active material concentration (mg/mL) | Sucrose (w/v) | Residual moisture (%) |
|---|---|---|---|
| 6A Ps | 6 | 4 | 2.09 |
| CRM for 6A Ps | 6 | 4 | 1.72 |
| 6A Ps-2 | 9 | 6 | 1.80 |
| CRM-2 for 6A Ps | 9 | 6 | 2.49 |
| CRM-3 for 6A Ps | 12 | 8 | 1.92 |
| 23F Ps | 6 | 3 | 3.4 |
| CRM for 23F Ps | 6 | 3 | 2.96 |
| 23F Ps-2 | 8.4 | 4.2 | 3.16 |
| CRM-2 for 23F Ps | 8.4 | 4.2 | 3.78 |
| CRM-3 for 23F Ps | 15 | 7.5 | 2.51 |

Residual moisture content from Lyo2 was significantly lower than from Lyo1 due to improved drying cycle. Secondary drying improves removal of bound moisture that is still present in the product even after all ice has sublimated. The secondary drying required a higher temperature (30° C.) than primary drying (15° C.).

At this point, the Lyophilizer total drying cycle time was 45 hours. Several parameters such as pressure and temperature were changed in order to reduce even more the drying cycle time (method: Lyo 3) Tables 9.1 and 9.2.

TABLE 9.1

Lyophilize Drying Cycle with increased Cabinet Pressure and Shelf Temperature (Lyo3)

| Drying | Cabinet Pressure (mTorr) | Shelf Temperature (° C.) | Time (hours) |
|---|---|---|---|
| Primary | 55 | 20 | 18 |
| Secondary | 55 | 30 | 5 |

TABLE 9.2

Karl Fisher Analysis for Lyospheres Dried in Lyo3

| Sample ID | Active material concentration (mg/mL) | Sucrose (w/v) | Residual moisture (%) |
|---|---|---|---|
| 6A Ps | 9 | 6 | 1.61 |
| CRM for 6A Ps | 12 | 8 | 1.64 |
| 23F Ps | 8.4 | 4.2 | 2.64 |
| CRM for 23F Ps | 8.4 | 4.2 | 1.87 |

Example 6

This example shows development of radiant energy vacuum (REV) dehydration (microwave vacuum drying (MVD)) conditions for producing polysaccharide (Ps) and $CRM_{197}$ (Pr; CRM) lyospheres.

Solutions of CRM and activated polysaccharides from serotypes 6A and 23F were prepared as described in Examples 3 and 4 and having Ps, CRM, and sucrose concentrations as shown in the Tables 10.1 and 10.2.

A modified Biomek FX pipetting robot (Cryomek) is used to dispense 50 µL aliquots of the solution onto the flat freezing surface of the Cryomek. A shoveling mechanism may be used to dispense the beads onto a small cold container without causing any fractures. After completing the cycle for each different solution, the beads are transferred into an intermediate storage container and kept at −70° C. until sublimative drying in a lyophilizer or by microwave vacuum drying. For microwave drying, beads were dispensed in single layers into the containers. Power, pressure and cycle time were set up. After drying the beads, lyospheres were stored at 2-8° C. (See Example 6 for specific parameters).

Two different MVD cycles were tested to dry the beads. For both cycles, the pressure was kept in the range of 50 to 60 mTorr. The temperature was dependent on much power was applied, staying in the range of 25 to 30° C.

TABLE 10.1

Microwave Vacuum Drying Cycle, MVD1 and MVD2

| Drying Cycle | Temperature (° C.) | Pressure (mTorr) | Power (W) | Time |
|---|---|---|---|---|
| MVD1 | 20-30 | 50-60 | 400-600 | 4 hours 30 minutes |
| MVD2 | 20-30 | 50-60 | 400-2000 | 6 hours 10 minutes |

TABLE 10.2

Karl Fisher Analysis for Lyospheres Dried in MVD1 and MVD2.

| Sample | Active material concentration (mg/mL) | Sucrose (w/v) | MDV1 Residual Moisture % | MDV2 Residual Moisture (%) |
|---|---|---|---|---|
| 6A Ps | 9 | 6 | 3.30 | 2.38 |
| CRM for 6A Ps | 12 | 8 | 2.94 | 1.72 |
| 23F Ps | 8.4 | 4.2 | 3.80 | 2.80 |
| CRM for 23F Ps | 8.4 | 4.2 | 3.01 | 1.83 |

MVD1 cycle took 4 hours and 30 minutes but it was not enough to reduce residual moisture content up to 2%. MVD2 cycle took longer with higher power and, therefore, it provided residual moisture content that was significantly lower.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for making a homogeneous solution of mutant diphtheria toxin (mDT) in anhydrous dimethyl sulfoxide (DMSO), the method comprising:
   (a) providing a dried composition of mDT; and
   (b) reconstituting the dried composition to a final concentration of 10 mg/mL or less in anhydrous DMSO by adding the anhydrous DMSO to the dried composition over a time period of two minutes or less and mixing for at least 10 seconds to provide a homogenous solution comprising the mDT.

2. The method of claim 1, wherein the dried composition is prepared by sublimative drying of an aqueous solution comprising the mDT wherein the sublimative drying is selected from lyophilization and radiant energy vacuum (REV) dehydration.

3. The method of claim 2, wherein the sublimative drying comprises freezing the aqueous solution in the form of cakes or lyosphere beads.

4. The method of claim 2, wherein the sublimative drying process comprises bulk drying performed in a container selected from the group consisting of metal tray, plastic tray, plastic bag, and class I tubing vials.

5. The method of claim 1, wherein the dried composition is prepared by sublimative drying of an aqueous solution comprising mDT to produce the dried composition, wherein the aqueous solution further comprises about 0.5% (w/v) or more sucrose and a buffer, and the sublimative drying is selected from lyophilization and radiant energy vacuum (REV) dehydration.

6. The method of claim 5, wherein the buffer is a Histidine, Succinate, MES, MOPS, HEPES, or Acetate buffer in a pH range of 5.0-7.0.

7. The method of claim 5, wherein the buffer is a Phosphate or a Citrate buffer in a pH range of 5.0-7.0.

8. The method of claim 1, wherein the dried composition has a moisture content of less than 6%.

9. The method of claim 1, wherein the mixing in step (b) is performed in 120 minutes or less.

10. The method of claim 1, wherein the homogenous solution comprising the mDT is conjugated to activated polysaccharides six hours or less following the reconstituting.

11. The method of claim 1, wherein the homogenous solution comprising the mDT has no detectable aggregation.

12. The method of claim 1, wherein the homogenous solution comprising the mDT has no detectable beta-sheet mediated aggregation.

13. The method of claim 1, wherein the homogenous solution comprising the mDT has no detectable beta-sheet mediated aggregation as determined by Fourier-transform infrared spectroscopy or dynamic light scattering.

* * * * *